(12) United States Patent
Buethorn

(10) Patent No.: US 7,618,387 B2
(45) Date of Patent: *Nov. 17, 2009

(54) FOOT ORTHOSIS SUPPORT DEVICE METHOD AND APPARATUS

(75) Inventor: Donald R. Buethorn, Ferndale, WA (US)

(73) Assignee: Cascade DAFO, Inc., Ferndale, WA (US)

( * ) Notice: Subject to any disclaimer, the term of this patent is extended or adjusted under 35 U.S.C. 154(b) by 161 days.

This patent is subject to a terminal disclaimer.

(21) Appl. No.: 11/351,872

(22) Filed: Feb. 10, 2006

(65) Prior Publication Data
US 2007/0191748 A1     Aug. 16, 2007

(51) Int. Cl.
- A61F 5/00 (2006.01)
- A61F 13/00 (2006.01)
- A61F 5/14 (2006.01)
- A43B 7/24 (2006.01)
- A43B 13/38 (2006.01)
- A61F 5/37 (2006.01)

(52) U.S. Cl. ............... 602/23; 602/1; 602/5; 602/6; 602/8; 602/27; 602/60; 602/61; 602/65; 602/12; 602/7; 36/140; 36/142; 36/143; 36/144; 36/150; 36/182; 36/88; 36/43; 36/44; 36/71; 128/882

(58) Field of Classification Search ............. 602/23, 602/1, 5, 6, 8, 27, 60, 61, 65, 12; 128/882; 36/140, 142–144, 150, 182, 88, 43, 44, 71
See application file for complete search history.

(56) References Cited

U.S. PATENT DOCUMENTS

| | | | |
|---|---|---|---|
| 4,981,132 A | | 1/1991 | Chong |
| 5,741,222 A | * | 4/1998 | Fiore ............... 602/27 |
| 6,602,215 B1 | * | 8/2003 | Richie, Jr. ........... 602/27 |
| 2005/0096576 A1 | * | 5/2005 | Castro ............... 602/27 |

* cited by examiner

*Primary Examiner*—Michael Phillips
*Assistant Examiner*—Tarla R Patel
(74) *Attorney, Agent, or Firm*—Davis Wright Tremaine LLP; George C. Rondeau, Jr.

(57) ABSTRACT

A corrective device to be worn on a human foot having a misalignment and positioned inside of footwear. The device having an inner shell having a first material composition and flexibility, and shaped to accommodate receiving therein and supportingly couple with the foot, and an outer shell having a second material composition and flexibility, the second material composition and flexibility being substantially the same as the first flexibility, the outer shell shaped to accommodate receiving therein the inner shell, supportingly couple with the inner shell and allow positioning into the footwear. At least a sufficient portion of a pressure is distributed by the outer shell and the inner shell over a desired area of the foot to provide an amount of correction to the misalignment while allowing the human to wear the inner shell inside of the outer shell inside of the footwear.

49 Claims, 17 Drawing Sheets

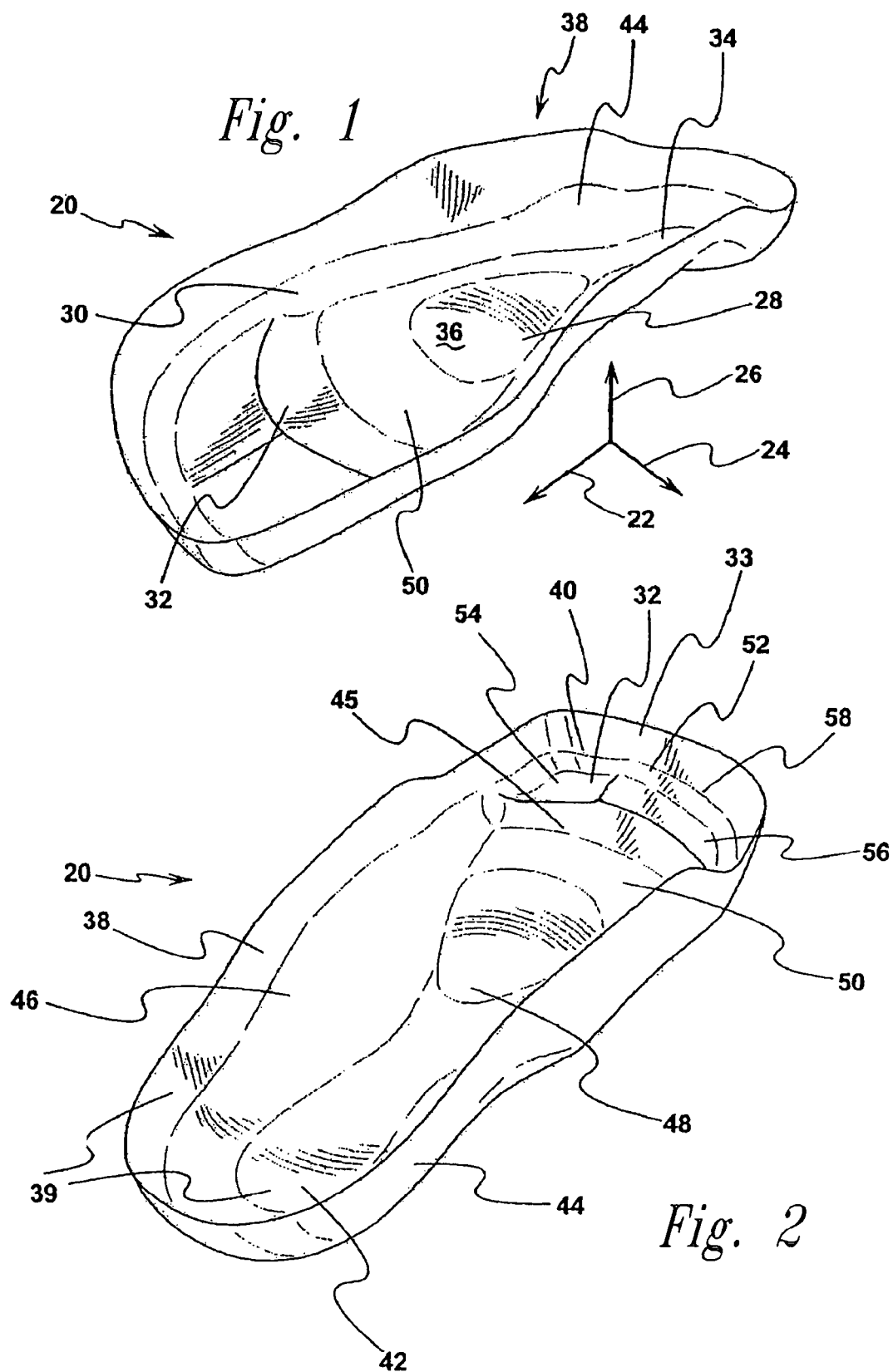

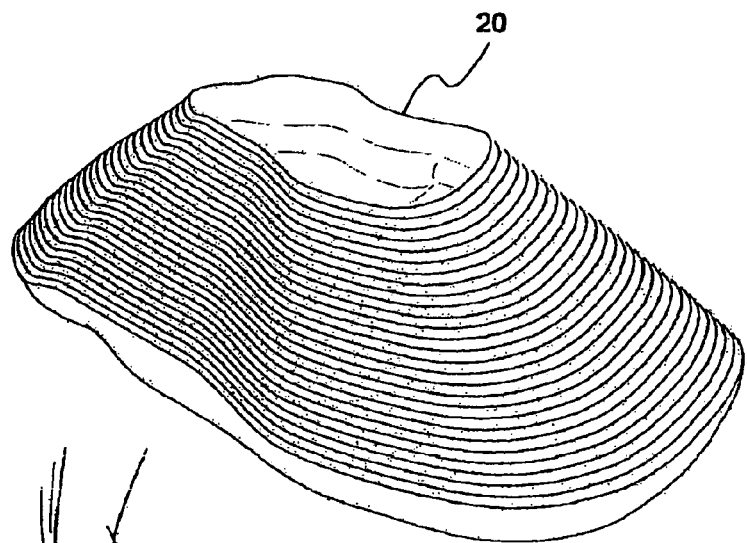
Fig. 3
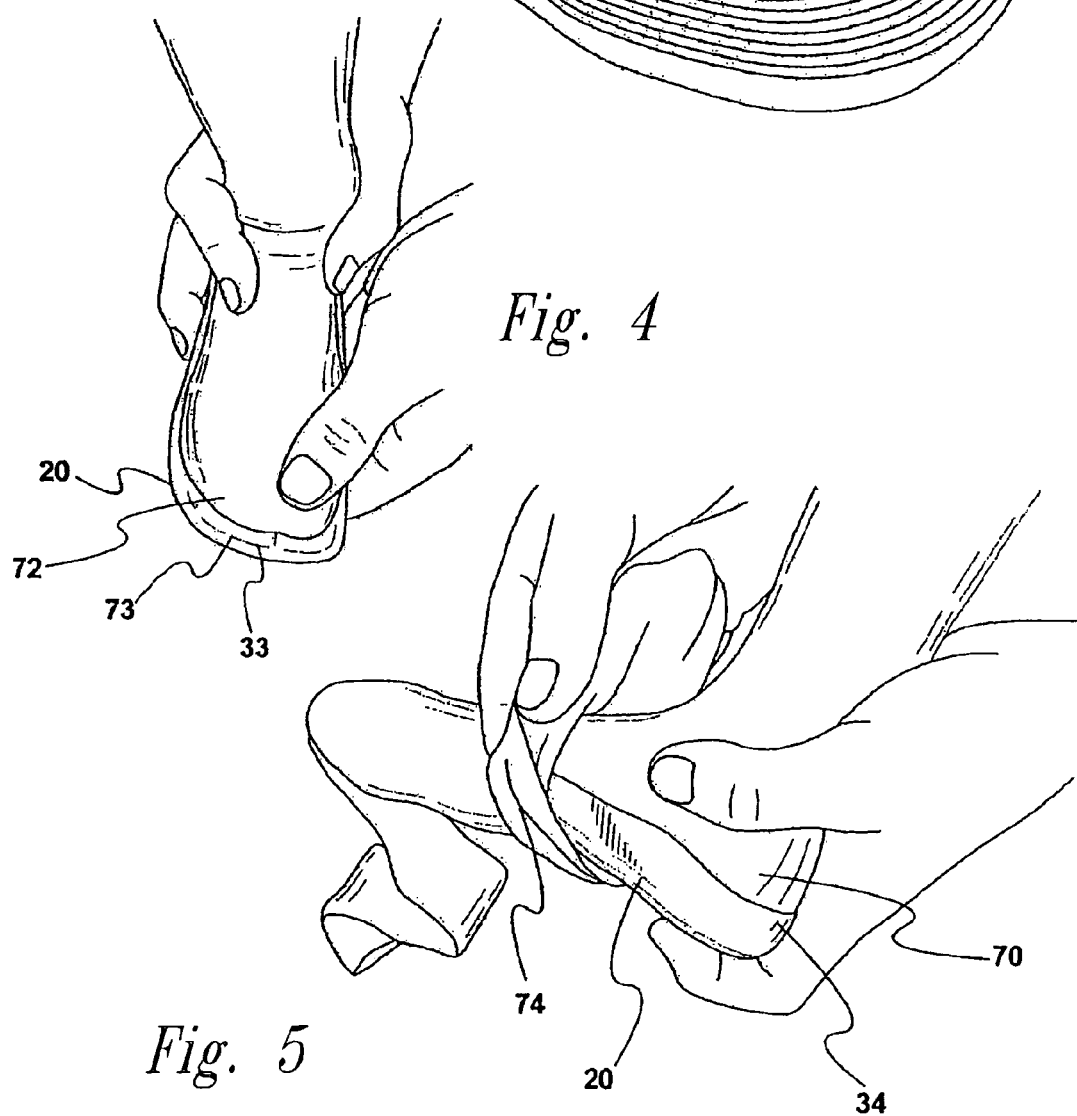
Fig. 4
Fig. 5

FOOT ORTHOSIS SUPPORT DEVICE METHOD AND APPARATUS

BACKGROUND OF THE INVENTION

Orthotics and lower limb orthosis devices, in one form, are made for patients by practitioners for a custom fit to accommodate a patients lower limb support needs. It has been found, in the practice of forming foot orthotics or orthoses, that the logistics of transporting product from the factory to the practitioner is time-consuming, as the practitioner must first send a mold back to the manufacturing facility. Further, there is an issue of maintaining product at the practitioner's location whereby constantly sending molds to the manufacturer can deplete the practitioner's supply of stock mold materials. Therefore, in one form it is desirable to have an embodiment where a semi-rigid device used to make a negative mold of a patient's foot is not sent back to the orthosis manufacturer, but rather, can be stored at the practitioner's location for reuse. Further, storage space is generally not plentiful at a practitioner's business location, and maintaining inventory of foot molding products can be very challenging. In one form, the embodiments below disclose a convenient method of storing and stacking the flexible members.

The description relates to a flexible support device that is adapted to be used in assisting in the molding casting process. In general, a negative shape of the patient's foot is cast for purposes of creating a dynamic ankle foot orthosis. It should be noted that the foot cast is for the lower leg including the ankle portion, as well as the lower foot region of a patient, essentially the biomechanical structures below the knee of a patient.

Another area of the disclosure relates to pediatric orthotics utilizing a flexible support device. In areas where custom orthotics are not appropriate for various budgetary reasons, a mild support system is advantageous for various young people with foot misalignments. Therefore, pre-made orthotics have provided a service where foot support is appropriate.

During pronation of a foot there are three significant segments of the foot that must be controlled. The heel area during pronation tends to shift into eversion. Eversion is an anatomical condition where the heel, with respect to the ankle, is repositioned and rotates about a longitudinal axis laterally outwardly. The longitudinal arch must maintain a proper biomechanical position and alignment. During pronation the arch moves medially and distally to a flat position, more so in the medial direction. Finally, the forefoot will shift laterally outwardly to abduction. Therefore, all three of these occurrences happen in conjunction and the heel and the arch in the forefoot will shift commensurate with the misalignment of each general foot region.

It should be noted that during collapse of the mid foot longitudinal arch, the skin surface of the heel will remain substantially intact with the weight-bearing surface, but the upper portion of the heel will move laterally inwardly, rotating about a substantially longitudinally extending axis.

Therefore, an effective orthotic or orthosis device must address all three of these simultaneously while providing for movement and general athletic motions of the patient. The device should address these misalignment issues and be comfortable and wearable by the patient.

A further embodiment of the invention is to have an off-the-shelf non-customized device for the patient as well. Further, because patients that are young are growing and outsize these devices in a relatively short amount of time, there is an economic incentive to make a less expensive device which will have a limited lifetime irrespective of the use and wear of the device.

Deep foot orthotics are problematic in that they have not often been comfortable to patients. Therefore, the challenge has been to provide a comfortable off-the-shelf foot orthotic that provides support and adapts to various patients' feet without specific molding.

Pre-made inserts have been problematic because of the instability associated with them.

BRIEF DESCRIPTION OF THE DRAWINGS

FIG. 1 is an upper front isometric view of a flexible support device.

FIG. 2 is an isometric view of a flexible support device showing the various regions of the device.

FIG. 3 shows an assortment of sizes of flexible support devices stacked in a convenient volumetrically efficient fashion.

FIG. 4 shows sizing of a flexible support device with respect to a patient's foot.

FIG. 5 shows a second stockinette positioned over the flexible support device and generally around the foot of the patient.

DETAILED DESCRIPTION OF THE PREFERRED EMBODIMENTS

Figure 15:
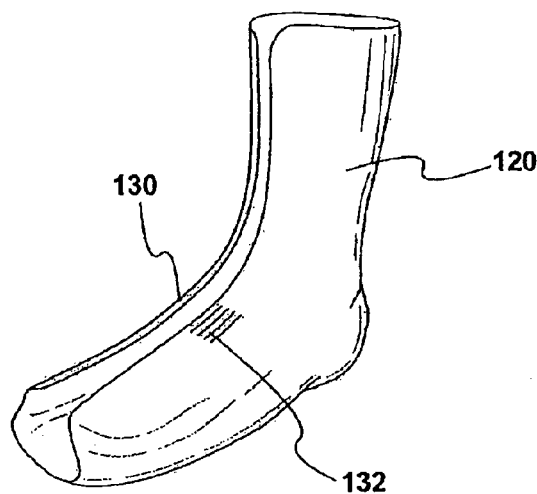
FIG. 15 is an isometric view of a rigid shell device.
Figure 19:
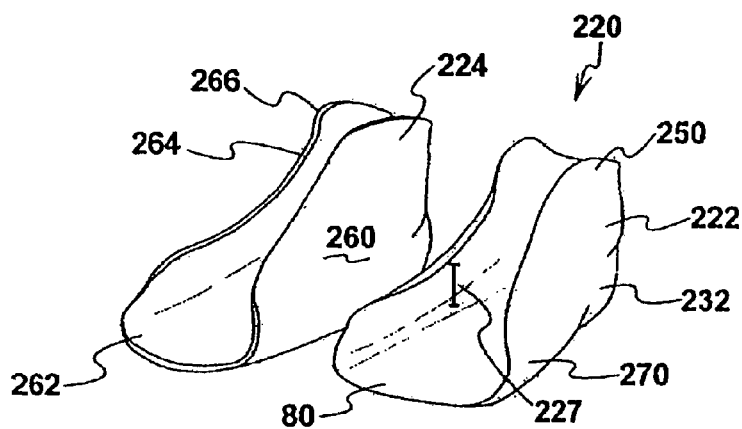
FIG. 19 shows an exploded view of an orthotic support device having a soft inner shell and a harder outer shell.
Figure 20:
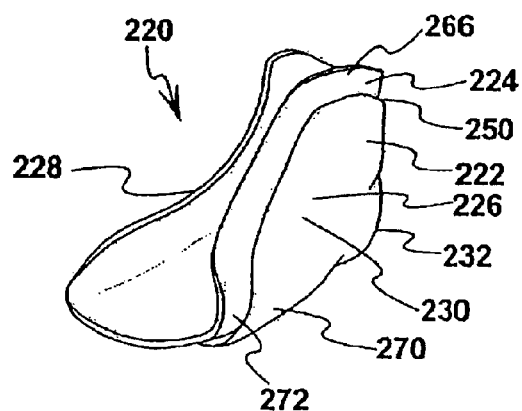
FIG. 20 shows an isometric view of an orthotic support with a soft inner shell having edge portions protruding beyond the edge portions of the outer shell.
Figure 21:
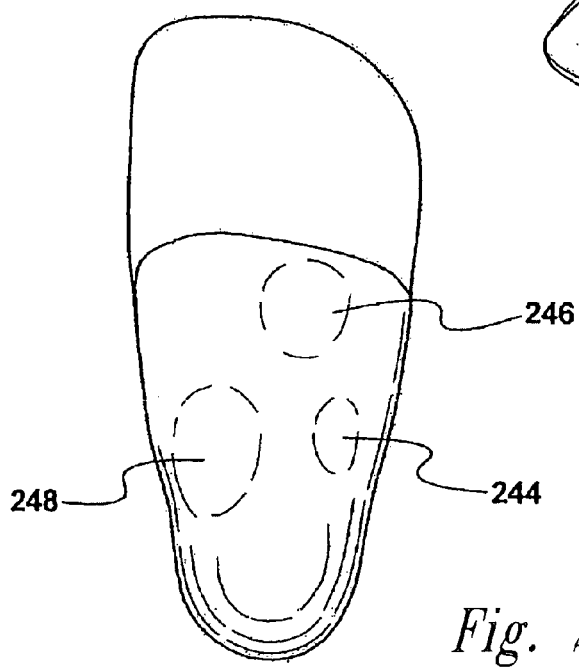
FIG. 21 shows a bottom view of an orthotic support device.

In general, the specification below will first describe one form of casting a lower limb orthotic/orthosis device whereby a flexible support device is employed. Thereafter, with reference to FIGS. 15-18, a second embodiment is shown whereby the second embodiment can be used in various forms to provide the practitioner numerous options for producing an orthotic/orthosis device. In general, the shell as shown in FIG. 15 can be used as a casting device, or alternatively as a measuring device to measure the general contours of a patient's foot where only the measurements need to be sent to a manufacturing facility for production of an orthosis (or simply used to provide a specific size and shape of orthosis premade). Further, the embodiments as shown in FIGS. 15-18 can be used in a modular-type arrangement were modular components are arranged to provide a wide variety and proper fit to the patient. Finally, the embodiments as shown in FIGS. 19-21 show a system where a rigid shell is employed with an interior soft shell, where in this version, the rigid outer shell is essentially the end product that provides support for the patient and the interior soft shell can absorb localized protrusions and indentations for a more comfortable fit for the patient.

As shown in FIG. 1 the flexible support member 20 is shown. As shown in this figure, an axis system is defined where the arrow indicated at 22 indicates a longitudinal axis. Likewise, the orthogonal arrow 24 indicates a lateral axis. Finally, the arrow that is orthogonal to the two mentioned arrows is indicating a vertical axis 26.

As further shown in FIG. 1, the flexible foot support 20 has a medial region generally indicated at 28 and a lateral region generally indicated at 30. Further, the longitudinally forward region is generally referenced as a distal region 32 and the opposed longitudinal region is commonly referred to as a proximal region 34. In addition to the aforementioned regions, a plantar region indicated at 36 defines the general upper surface that comes in contact with the lower portion of a patient's foot. The medial lateral wrap region generally indicated at 38 is a substantially vertical region that is adapted to encompass the calcaneus (a portion of the heel bone), the medial arch which is sometimes referred to as the longitudinal arch, and the navicular. Further, the medial lateral wrap region is adapted to cover the first metatarsal head and the fifth metatarsal head, the base of the fifth metatarsal head and the peroneal arch.

As shown in FIG. 2, the plantar region 36 is approximately defined as the central region within the encompassed section 40. The hatched region around the upper perimeter is substantially defined as the medial lateral wrap region as described above. The plantar region 36 is defined to have various regions as shown in FIG. 2. Beginning in the longitudinally rearward section, the heel depression indicated at 42 is defined as a region adapted to be depressed to a patient's heel during a molding process. The heel depression region 42 provides a foundation for the medial lateral wrap region 38 as described further below and this region of the material is adapted to work in conjunction with this longitudinally rearward portion to correct various skeletal biomechanical misalignments such as pronation, supination, and varus-valgus. The peroneal arch is a region 44 where the surface raises somewhat vertically. The peroneal arch is distal to the heel depression to help control the heel (calcaneus position), and is right behind the base of the fifth metatarsal. This region helps support the arches of the foot and overall foot alignment. It should be noted that the peroneal arch region 44 is a vertical indentation which is represented in the outer surface of the flexible support devices 20. This can be advantageous for providing feedback to a practitioner when casting to denote a certain position. Further, the region 44 is a potential reference point to aid instruction when instructing a practitioner to properly exercise a molding process and aligning the bone structure of a patient described further herein below.

Also shown in FIG. 2, the medial arch region 46 is defined generally as a raised region in the central portion of the plantar region 36. As with the peroneal arch region 44, the medial arch region has a raised region which a practitioner can use to grab when conducting and creating a mold upon a patient as described further herein below. The flexible support member 20 by default has a raised medial arch region. It should be noted that the member is flexible and described further herein below. The medial arch is useful in aligning the avicular navicular and assisting in properly aligning the foot to a solid functional biomechanical neutral position as opposed to a pronated foot or supinated foot. The metatarsal arch indicated at 48 is a raised region adapted to support the metatarsals, particularly the central metatarsals 2, 3 and 4.

Further shown in FIG. 2 is the metatarsal depression generally indicated at 50. This region is defined as a region that supports and aligns the metatarsal heads.

The most forward distal region indicated at 52 is the toe rise region. This region is divided into a drop first toe subregion 54 and a two-five subregion 56. The drop toe subregion 54 is positioned slightly vertically lower with respect to the two-five subregion 56. From the sulcus, the two-five subregion 56 slopes downwardly in the longitudinally forward direction toward the distal area and downwardly to the laterally outward region indicated as 58. This region helps align the foot and allows propreaceptive input for the client so that the foot may be aligned properly. Specifically, the surface allows the client to become aware of his feet and his foot placement. Therefore the raised region brings this awareness to the client during the casting process, allowing for a better mold.

There will now be discussion of the molding process, during which a practitioner will take a mold of the lower foot region of a patient. As shown in FIG. 3, the first step in the molding process is to choose the proper size of a flexible support device. FIG. 3 shows an assortment of sizes of flexible support devices to accommodate a wide variety of patients. As shown in this figure, the variety of flexible support devices 20 are adapted to be stacked as shown. In other words, the cavity region of a larger flexible support device will support the next smaller size. In a storage location, the flexible support devices are arranged in a stacked position whereby an outer surface of an immediately smaller flexible support device is engaged in a cavity region of the immediately larger flexible support device so the plurality of flexible support devices are arranged in a stacked manner. This allows for storage of quite a few flexible support devices in a practitioner's office. Further, this stacking method facilitates in sizing up the proper flexible support member 20 so the practitioner can easily identify which size would be appropriate. For example, if the practitioner chooses one of the central sizes and it is does not properly fit the patient, the practitioner can gauge the difference of size required and skip a set number of increments smaller or larger to gauge the approximate appropriate size for the particular patient.

Thereafter (or prior to sizing), a stockinette is placed on the patient's foot as shown in FIG. 4. A stockinette is defined broadly as a flexible cover to provide some protection and at least partial separation between respective inner and outer portions of the stockinette. In one form the stockinette is made from a fabric-like material, similar to an expandable sock. The foot is then placed into a properly sized flexible support device 20. The various plantar surfaces described above with reference to FIG. 2 must be aligned with the corresponding anatomy of the patient's foot. In particular, the heel region of the patient should be pressed firmly against the substantially vertical surface of the proximal region 34 of the medial lateral wrap region 38. Referring back to FIG. 2, the proximal location of the medial lateral wrap region 38, generally indicated at 39, is referred to as the heel cup region. One advantageous aspect of the heel cup region 39 is that it provides an initial foundational support when molding. When not providing a vertical support region in the heel cup region, the prior art support members will move with respect to the foot to improper locations. This leads to improper casting and an eventual poor support device. Therefore, having the heel cup region 39 aids in preventing an improper casting.

Now referring to FIG. 5, it can be seen that the heel region 70 of the patient is pressed firmly against the heel cup region 39 of the flexible support devices 20. After the heel is properly aligned in the rearward, proximal location of the flexible support device 20, the practitioner must check the distal regions to ensure that the metatarsal heads are not crossing the total sulcus. Referring back to FIG. 2, the total sulcus indicated at 45 is the distal methead proximal toe rise area indicated at the laterally extending line designated by 45. Although other portions of the anatomy could be aligned to the flexible support device, this region is accessible to view by the practitioner and generally, the intermediate plantar surface regions will be properly positioned corresponding to the anatomy of the patient. Referring back to FIG. 4, it is advantageous to have the overall length of the flexible support device slightly longer than the toes 72 of the patient. In other words, this region is not critical for a proper mold and therefore the extra space indicated at 73 between the toes 72 and the forward vertical region 33 will not generally be a problem in molding. In one form, the gap region between the forward surface of the patient's toes 72 and the forward vertical region 33 is approximately a quarter of an inch or greater.

FIG. 5 further shows the application of a second stockinette 74. In one application, a second stockinette is applied over the flexible support device 20 and the initial layer of stockinette. The second layer of stockinette is advantageous for removal of the layer of the cast that is to be applied which is described below. Further, it has a second advantage of aiding the removal of the flexible support device 20 after the mold has at least partially cured and taken a substantially rigid form (also described further below). Further, the second stockinette 74 increases the net volume of the positive mold which represents the foot and ankle region, the first and second stockinettes and the flexible support device 20.

Figure 6:
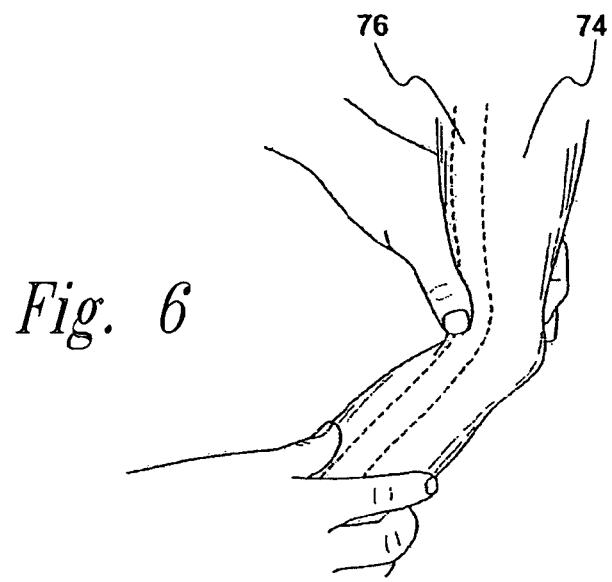
FIG. 6 shows positioning of a member that aids in the prevention of injury when removing a cast.

As shown in FIG. 6, a cutting strip 76 that is shown beneath the second stockinette 74 is "wormed in" down a portion of the patient's leg and foot region. In one form, this is located in the forward central region to facilitate a buffer region when removing the mold. This cutting strip is applied underneath one of the two stockinettes. In another form the cutting strip is applied in the outer surface of the stockinette 76. Applying the cutting strip 76 is an optional process for aiding in the removal of the mold if a non-flesh-cutting element is used to remove the mold. It in another version, the cutting strip is taped or otherwise attached to the inner stockinette.

Figure 7:
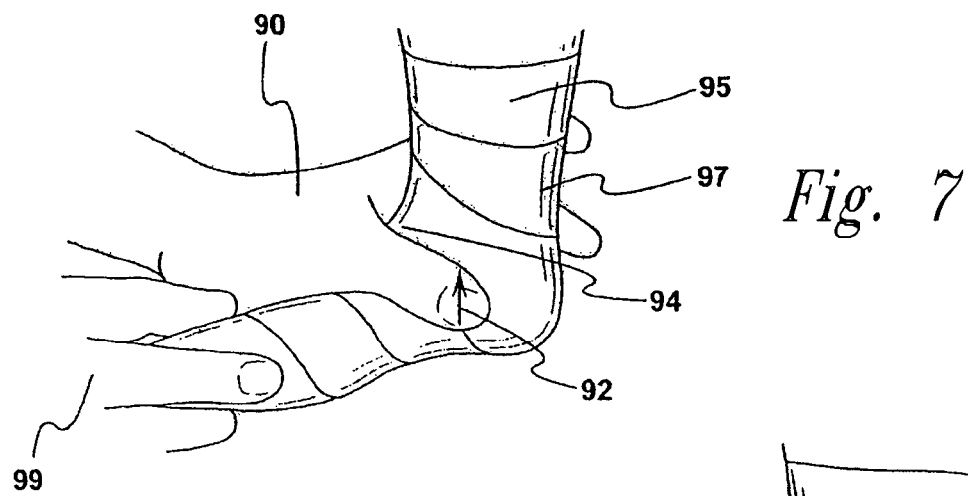
FIG. 7 shows flexible strips in a flexible state wrapped around the foot of the patient.

As shown in FIG. 7, pliable molding strips 95 are wrapped around the second stockinette 76 (see FIG. 6) in one form the molding strips are fiberglass, but any substance that is initially pliable and can harden to a mold after a few minutes would suffice. The preset state of the fiberglass rolling is generally a condition where the fiberglass tape is wet and wrapped around the entire ankle foot region with the stockinette applied thereon as shown in FIG. 6. The molding strips 95 are defined broadly to cover all materials that have the ability to be applied in a very flexible form fitting manner and harden to at least a semi-rigid state to preserve a negative mold of the outer surface of the inner structure members (e.g. the contour of the lower limb and the flexible support device). When the molding strips are all applied to the foot region they collectively form a wrap 97 as shown in FIG. 7.

Before the wrap 97 hardens, the practitioner engages in an alignment and feature definition process. This process essentially positions the foot into a proper neutral biomechanical position to form a proper mold. As described above, the features of the flexible support device 20, given its flexibility, allow the practitioner to have a greater amount of control over the manipulation of the position of the various features of the foot and lower limb regions of the patient. In other words, without some flexibility of the flexible support device 20, the anatomical features of the foot would not be manipulated. However, the flexible support device is sufficiently rigid to allow a distribution of pressure upon adjacent regions of the foot and lower ankle region that the practitioner is not in direct contact with. The goal is to have the mold formfitting to the contours of the patient's foot and maintaining the correct overall biomechanical alignment.

The aforementioned arch regions as shown in FIG. 2 assist in aligning the arches to form a proper mold. As shown in FIG. 7, the hindfoot is stabilized with the hand indicated at 90. The thumb is on the navicular bone of the patient and supply a vertical force indicated by arrow 92 helps to define a longitudinal arch. The fingers span the instep region 94 and the forward tip portions of the practitioner's fingers grasp the calcaneus region and in some cases help remove the pronation of the patient. If the patient does not have a pronation problem, the left-hand 90 will support the ankle region so it is properly neutrally aligned. The palm of the hand 90 is on the medial side of the foot and the fingers extend around the back of the heel.

The practitioner's other hand 99 of the practitioner brings the forefoot to the neutral position. A neutral position must be executed about a longitudinal axis so the portion of the foot is properly positioned. Further, the medial and lateral alignment must be properly aligned as well. It is important to keep the heel vertical, therefore there may be some sacrifice in keeping the forefoot horizontal in order to properly align the heel region of the patient's foot. The heel alignment is the base, and given the individual's range of motion, the best biomechanical alignment is obtained. The flexible support device provides a more gradual transition from the forefoot to the rear foot because the rigidity and flexibility of the flexible support device 20 will allow any manipulation to extend longitudinally rearwardly and supply a force along the surface of the foot. In other words, even though the practitioner will exert a force on the distal region of the foot, this force is distributed longitudinally rearwardly to the heel region because of the flexibly controlled deformation of the flexible support device. Without the flexible support device 20, any manipulation by the practitioner's fingers will create a localized depression upon the wrap 97. However, with the flexible support device contained thereunder, any manipulation is not directly applied but it is more uniformly distributed around the adjacent regions were pressure is applied. Given that the flexible support device already has a preset form of key features and depressions as described in FIG. 2, these features are better maintained. The flexible support device provides a more natural transition of manipulation from the rearward portion of the foot to the forward portion of the foot.

Figure 8:
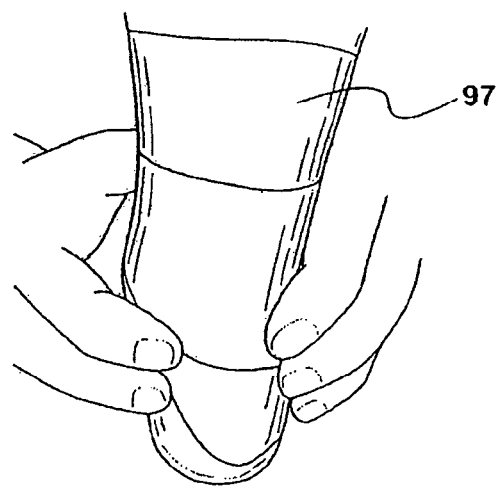
FIG. 8 shows the practitioner positioning the ankle region of the patient for proper alignment.

As shown in FIG. 8, the process of the alignment and feature definition process is substantially complete and the wrap 97 is beginning to cure to some degree and taking a solidified form. At this point the practitioner has the ability to manipulate localized regions for a better detailed fit. As shown in FIG. 8, the practitioner is contouring the heel to a proper alignment. Of course the practitioner may choose to contour other regions to take a proper neutral biomechanical set form. It should be noted that when pressure is applied the medial lateral wrap region 38 as shown in FIG. 2, the precured wrap 97 disperses pressure and aids in not allowing "flesh displacement". In other words, particularly in younger patients with more "fleshy" feet that contain greater fat deposits, the medial lateral wrap region 38 allows a more proper distribution of pressure when the wet flexible wrap 97 is applied therearound. The flexible support device 20 having a central chamber region aids in positioning the patient's foot from the beginning of the molding procedure. In other words, instead of having a substantially planar device without sidewalls, the medial lateral wrap region aids in initially positioning the foot so the margin of error is reduced for the alignment of the various arch and depression regions 42-50 discussed in FIG. 2 and the corresponding anatomical portions of the foot. The patient's foot is channeled into this chamber region and there are less manipulation and alignment issues for the practitioner to be concerned with when performing the mold.

Figure 9:
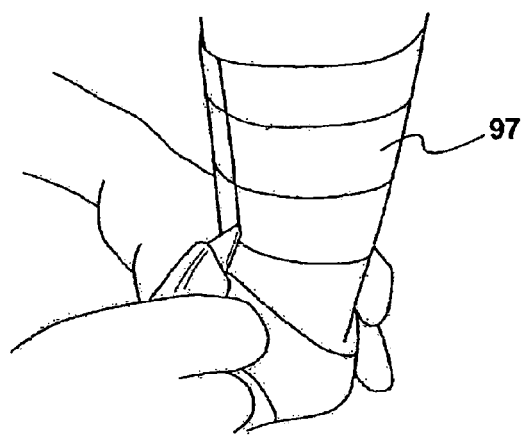
FIG. 9 shows a method of removing the cast from the leg of the patient.

As shown in FIG. 9, the cast is removed by incising the front portion with any conventional type of tool. Any particular chosen method of cutting the cast after it has cured can be employed. It should be noted that the flexible support device 20 aids in the removal of the cured cast from the patient's foot because it allows for a distribution of pressure around the lateral regions of the foot during removal. The flexible support device 20 further minimizes distortion during cast removal when the forward central region of the cast must be expanded and pried laterally outwardly to allow the foot and ankle to be interposed and removed therein between the cut portion. Minimizing the deformation of the cast is useful when the cast is not fully cured, which can be a problem when colder water is used when beginning the curing process of the cast, or other reasons that may lead to a slow curing process.

Figure 10:
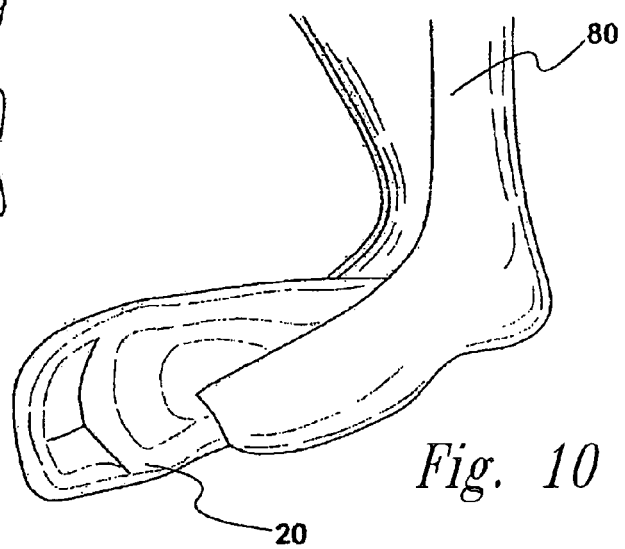
FIG. 10 shows removal of the flexible support device from the cast.

FIG. 10 illustrates one particular use of the flexible support device 20. As shown in this figure, the flexible support device 20 is removed from the cast 80. This allows for reuse of the flexible support device. This removal can be executed by the practitioner and the practitioner can thereafter properly store the flexible support device in the manner as shown in FIG. 4. This is particularly advantageous because in one form of prior art practice, the entire cast is sent to a third-party company which makes the final orthosis support device. This allows the practitioner to refrain from sending support devices adapted to be positioned on the lower portion of the patient's foot to be mailed along with the cast to a third party fabricator. This depletes the supply of support devices for the practitioner, who makes the cast at a location which is generally not the location where the final orthosis support device is created. Therefore with the present invention, the practitioner maintains his supply of the flexible support devices as shown in FIG. 4.

Figure 11:
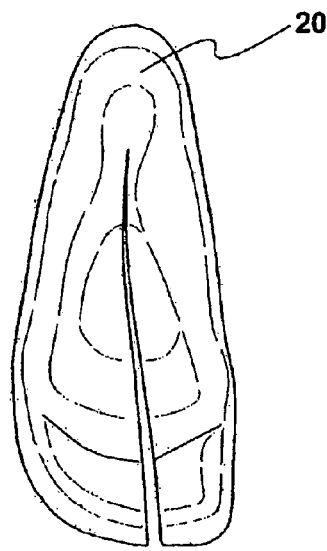
FIG. 11 shows a method of altering the flexible support device to accommodate a patient with a narrow foot.
Figure 12:
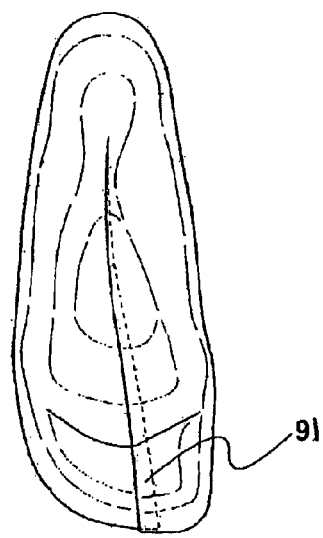
FIG. 12 shows a method of overlapping the flexible support device to accommodate a narrower foot of a patient.

There will now be a discussion of various adjustments that can be made during the molding process with initial reference to FIG. 11. As shown in this figure, the flexible support device 20 is incised in a substantial longitudinal direction. Now referring to FIG. 12, the flexible support device can be overlapped at the region indicated at 91 to provide for a patient's foot that may be narrower in the lateral direction. This provides flexibility for various shapes feet of patients. It should be noted that when a shorter and wider foot is required to be molded, the medial lateral wrap regions 38 have a certain amount of flexibility to allow this wider foot to be contained in the chamber region of the flexible support device 20. The support infrastructure of the various interior surfaces described on FIG. 2 is maintained even when a wider foot is entered in the chamber region of the flexible support device 20.

Figure 13:
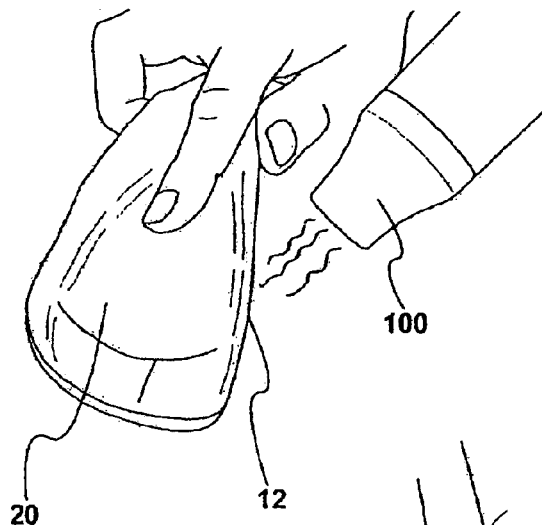
FIG. 13 shows a method of repositioning the flexible support device by applying heat to a localized area.
Figure 14:
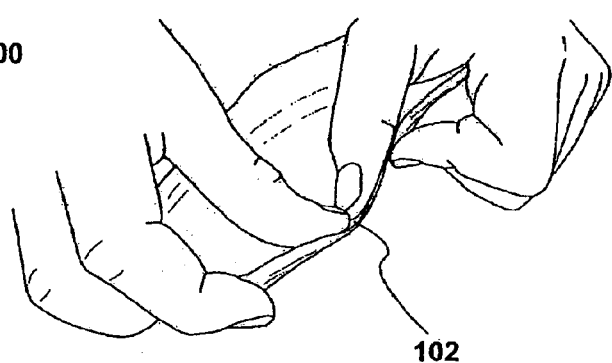
FIG. 14 shows alteration of the flexible support device to accommodate a particular patient.

In the situation where there are bony prominences or extreme shapes of a patient's foot which require special accommodation, reference is made to FIGS. 13 to 16. As shown in FIG. 13, a heating element 100 supplies heat to a specific location of the flexible support device 20. It should be noted that any area of the flexible support device can be heated and manipulated to accommodate any specific situation with a patient. It is often at the discretion of the practitioner to accommodate various extreme anatomical features of the patient, or any disfigurements. Therefore, by way of example, a formation process is shown in FIGS. 13-16. FIG. 13 shows the heating of the medial region where the first prominent method would be slightly extruded on the patient. As shown in FIG. 14, the region 102 is biased laterally outwardly to accommodate this feature of the patient. Of course various methods of alteration are available, such as an alteration to the flexible support member 20, where the base of the fifth metatarsal bone region is heated so the material becomes plastic and formable where the practitioner can manipulate the region outwardly to accommodate an outward extension of the patient's foot in this region.

It should be noted that the flexible support device 20 is particular adapted for external posting. During this process, shim-like devices are positioned either externally of the wrap or in some cases wrapped internally thereunder. The shim-like devices provide a consistent support surface for maintaining the foot position in a certain natural alignment positioned for molding. As described above, the application of pressure of the shim allows for a more consistent natural transition of forefoot to rear foot, given the rigidity of the flexible support device and the flexibility of the device as well. It should further be noted that the various features as shown in FIGS. 1 and 2 provide assurance that the internal arches of the patient's foot are maintained in the manipulation of the patient's foot during the molding process.

The embodiments as shown in FIG. 15 relate to a rigid outer shell device (control module 120) that can be used for casting or only as a measuring device for determining proper orthoses for the lower leg. In general, the full lower shells comprise a support module shown in FIG. 15 having an approximate section that extends up above the ankle. This is made of a flexible material such as plastic in a similar manner as the flexible support device 20 described above and has a central slit region that allows for it to be adjustable. The key features are molded into this module, such as an arch or other anatomical regions as described in shown in FIGS. 1 and 2. Further, prominent features of the foot are compensated for as well.

In one form, the control module 120, which is one form of a flexible support device, can be used to assist in casting whereby modules are placed around the patient's foot and squeeze tight for proper fitting. Thereafter, the practitioner, using standard mold casting techniques that are described above, is able to create a correct negative cast of the patient's foot. Thereafter, this cast is sent to a facility (or executed on site) whereby the control module is a known fixture of a cast and making an improper positive model of the patient's foot can be avoided. Thereafter, there is a positive model (mold) that is used to create an orthosis support device.

It should be noted that it is advantageous to have the lateral lower portion extend over the foot as well as have the proximal section extend up the lower calf of the patient to control foot position during the casting.

A second application is to use the control module as a sizing shell, whereby no casting is conducting by the practitioner, but the particular size of the control module is relayed back to the manufacturer of the final braces to eliminate casting and the physical mailing of the cast which is expensive and causes a time delay.

Figure 16:
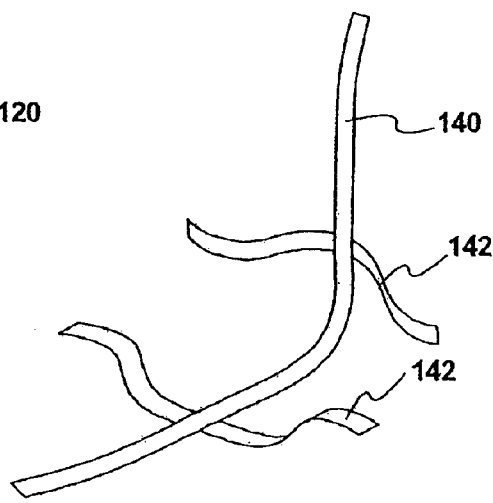
FIG. 16 schematically shows another device adapted to measure the lower limb portion of a patient.

To facilitate the communication of the proper sizing of the foot without taking a cast, marking indications, such as shown in FIG. 15, can be employed whereby the ridge 130 will engage certain coinciding locations with certain markings 132 which would be indicated by certain measurements. As shown in FIG. 16, this could be accomplished with a strap like system having a base support 140 having a plurality of flexible measuring devices 142.

Figure 17:
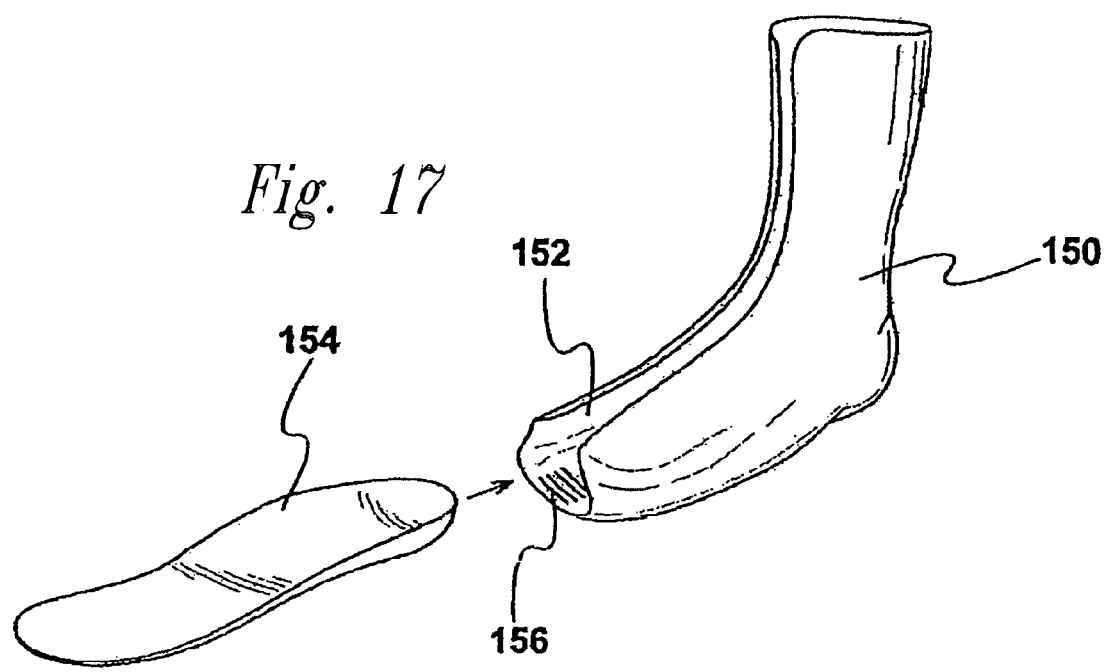
FIG. 17 shows a casting device operating in conjunction with an insert adapted to cooperatively function in a manner to get a proper measurement of the foot of a patient.

Another element of the apparatus is to have modular components as shown in FIG. 17. As shown in this figure, there is a rigid foot structure component 150 having a central lower cavity region 152 that is adapted to receive an orthotic-like insert 154. The theory is that the practitioner can fit the shell to the patient and further have the flexibility of fitting one of the stock orthotic molds to the patient as well. The shell can have various lines 156 or other adjustment features to quantify the position and orientation of the orthotic-like insert 154.

Figure 18:
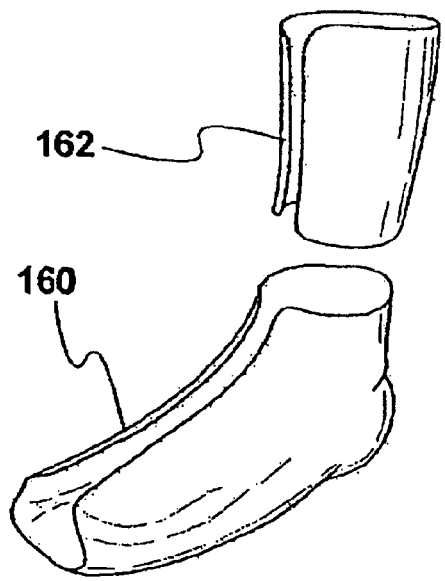
FIG. 18 shows another modular arrangement of devices adapted to properly measure the lower limb of a patient for purposes of creating an orthotic or orthosis.

As shown in FIG. 18, the modularity can further extend to having a lower semi-rigid fitting module 160 and then an upper semi-rigid module 162. These modules can work in combination and be taken from a plurality of modules that could be stacked in a manner similar to FIG. 3 to properly fit the patient.

This concept can be taken further to having an off-the-shelf type orthotic with mix-and-match components to properly fit the patient.

Now referring to the embodiment shown in FIGS. 19-21, the apparatus 220 comprises an outer support shell 222 and an inner liner 224. In general, this embodiment employs a rigid shell to provide a proper orthosis devise for the patient and further uses an inner soft shell liner to accommodate various bio-structural variations between patient to patient. In general, this embodiment does not employ casting, but rather the plastic shell itself is provided as the end product for the user to wear for lower limb support.

The outer shell has an interior chamber region and the inner liner has an exterior surface that is adapted to engage the inner surface of the outer shell 222. The outer support shell 222 comprises a perimeter support region 226 having medial and lateral sections 228 and 230. The outer support shell 222 further has a heel cup 232 in the rearward portion of the apparatus 220. The perimeter support region 226 is positioned in a location that is an approximate support location for the patient. In other words, the outer shell provides a rigid support to control the biomechanical positioning and alignment of the patient.

The outer support shell is made of a rigid material such as plastic, but does provided a certain amount of flexibility or comfort to account for various foot positions which the patient may be in without allowing the foot to completely collapse.

The embodiment shown in FIGS. 19-21 is adapted to be an off-the-shelf type orthotic utilizing proprioceptive feedback (sensory feedback); this is important in providing the patient with a heightened sense of foot position to aid in proper alignment of his or her feet.

The perimeter region 226 provides a certain amount of flexibility; when it is depressed by hand with a modest grip, the size will deflect inward or outwardly a few millimeters. It is important to note that this flexibility provides functionality for accommodating a wide range of patients' feet. Further, the flexibility allows for a footwear device such as a shoe or a boot to press upon the outer surface of the outer support shell to provide a better and more accommodating fit. The outer support shell 222 has an overall thickness between 0.5 and 3 millimeters in the broader range. A more preferable range is between 1/16 of an inch to 90 thousandths of an inch. In one form, a polyethylene base plastic is used to mold the outer support shell 222. Of course other materials providing flexibility and strength can be employed.

As shown in FIG. 21 the under portion of the outer support shell 222 comprises a variety of support sub region surfaces. It should be noted that this underside of the surface correlates to a raised region on the chamber region of the outer support shell 222. As shown in this figure, the peroneal surface 244 is located on the laterally outward region; the metatarsal raised region 246 is located in the forward medial region and adapted to engage the metatarsals of the patient. The medial longitudinal arch indicated at 248 is adapted to provide the common support in the laterally inward medial region of the patient. These arches are accentuated to some degree to give proprioceptive feedback to the patient so he or she will be induced to mentally align his or her foot to enhance his or her development of voluntary control of foot alignment.

As shown in FIG. 20, the outer support shell 222 has a rearward upper perimeter ridge region 250. This region is positioned vertically below the perimeter ridge 266 of the inner support liner to provide a blending of pressures from the perimeter region 250. In other words, by positioning the perimeter ridge 266 above the lower rigid ridge 250, less direct edge pressure is applied to the foot region of the patient. The inner liner 224 provides the smooth transition to prevent that focused edge pressure that would otherwise be present and create discomfort with the patient. The upper portion of the inner liner allows for an automatic adjustment of the pressure, so the upper perimeter ridge region 250 need not be custom to the patient; rather, the apparatus 220 is self-adjusting to each patient.

The inner liner 224 protects the side of the foot as it shifts positions from the proximal edge of the support shell. In other words, the patient is less likely to engage the perimeter rigid region 250 and have their flesh have a localized pressure developing an irritation.

There will now be a description of the inner liner 224 with initial reference to FIG. 19. As shown in this figure, the inner liner 224 comprises a base region 260 and a forward region 262. The inner liner 224 further has an upper region 264 that comprises a perimeter ridge 266. The construction of this inner liner 224 is generally made from foam. In one form, the inner liner 224 is made from closed-cell 5-pound density foam from ethylene vinyl acetate.

The forward region of the outer support shell 222 has a lateral region 270. As shown in FIG. 20, the inner liner 224 has an extension region 272 that extends longitudinally forward from the lateral region 270. The inner liner 224 is adapted to extend out and cover the metatarsal head. The support shell is adapted to be terminated just prior to the fifth metatarsal head on the lateral side. It should be noted in FIG. 20 that the medial side is adapted to be cut back before the first metatarsal head.

By having the outer support shell 222 provide the rigid structure so the extension region 272 is positioned at substantially right angles from the lateral region to the plantar region, the inner shell provides some rigidity to prevent abduction of the foot when the foot pronates. This is a condition when the medial longitudinal arch of the patient collapses.

Now referring to FIG. 19, the general area indicated at 80 is defined as a pivot region where the metatarsal heads approximately end and, in an operating environment, the patient will pivot when walking or running. It should be noted that the lateral region 270 terminates prior to this pivot region 80 to not interfere with the pivoting action. However, the region 272 of the inner shell 224 being more flexible and made from foam-like material will accommodate the pivoting action during walking or running (or other bipedal motion).

Therefore, it can be appreciated that the apparatus 220 is well suited to prevent pronation of a patient's foot which is a common joint misalignment biomechanical issue in many young patients. The medial section 228 of the perimeter support region 226 will have a tendency to apply a pressure on the medial region to prevent the pronation described above. Further, with the cup region orientated where the rearward surface extends in a plane that is substantially orthogonal to the longitudinal axis and the medial region in a plane orthogonal to the lateral axis, additional support is provided and added rigidity is a benefit to prevent eversion of the heel.

The depth allows the flexible support shell to function properly because having the vertical region indicated at 227 in FIG. 19 allows for a greater moment of inertia when a moment is applied about a lateral axis such as a pressure from the patients foot in the lateral region 270. This is particularly advantageous because less material and structure is required to provide that rigidity, creating a lighter more compact orthotic.

The final component of providing a proper biomechanical alignment for the patient is preventing the forefoot from abducting laterally outwardly with respect to the heel region of the patient. As described above in greater detail the lateral region 270 provides a base region for supporting the portion of the inner liner extension region 272 to aid in supporting in controlling the abduction. As described above, the flexible foam insert provides flexibility during running where it will actually collapse to a certain degree to provide the range of motion for the patient.

The apparatus 220 is particularly useful in an environment of footwear such as a shoe where the upper perimeter ridge 266 of the inner liner 224 is adapted to position laterally outwardly with respect to the center chamber region of the shoe. In other words, the extension region 272 is easily repositioned and grasped laterally outwardly by the patient and the perimeter region of the patient's foot will easily glide past the outer support shell 222 and be positioned in proper foot position in the shoe. It should further be noted that given the overall length of the apparatus, it will fit properly in a shoe and not be positioned vertically forward with respect to the shoe to prevent movement of the soft liner inner liner 224.

In one form, a layer on the upper surface of the inner liner 224 can be applied to aid in breathability of the apparatus 220. Further, the coefficient of friction between the foot and stocking of the patient can be adjusted to prevent discomfort such as excessive footwear which may cause blisters or the like.

A further modification can be employed where the lower surface of the outer support shell 222 can be filled with some form of material to provide extra support and rigidity. In one form, the aforementioned arch regions can be enhanced and amplified to facilitate the proprioceptive feedback to the patient.

One form of manufacturing the outer support shell 222 is employing common thermal sheet forming techniques such as draping. However, many forms of manufacture can be employed such as injection molding, milling etc.

Various orthotic support device implementations include outer support shells and inner support shells being formed from the same or similar material. In general, these same or similar material implementations use various shapes of inner and outer shells made from materials such as plastics, polymers, composites, ethethlyenes, vinyls, or other sorts of materials that provide a desired combination of flexibility and rigidity for the shells. Materials for the inner and outer shells are selected to have substantially the same or similar material compositions with same or different thicknesses to provide sufficient orthotic support and/or manipulation and adequate flexibility to allow for a certain desirable degree of user comfort when particular inner and outer shells are coupled to form an orthotic support implementation.

Some of the implementations using substantially the same or similar materials for both the inner and outer shells can vary the thicknesses of the inner and outer shells to allow for further adjustment of the balance between degree of orthotic support and/or manipulation and user comfort levels. The thicknesses of the inner and outer shells are substantially the same in some illustrated embodiments, but can be of different thicknesses if desired or can be. In one embodiment. The thicknesses can also be varied throughout a particular shell as the balance of the degree of orthotic support and/or manipulation and the user comfort level may be varied in different locations of the orthotic support implementation.

In some implementations the materials used for the inner and outer shells can be different, but both the inner shell and the outer shell have a similar quality of rigidity and flexibility. In these implementations, even though the inner and outer shells are made from different materials, both the inner and outer shells share similar compressibility characteristics with similar levels of resistance to compression forces.

Three exemplary versions of these implementations using inner and outer shells having substantially the same or similar materials or having different materials with similar compressibility characteristics are shown in FIGS. 21-31. The exemplary versions generally differ by the extent that their inner shells contact and subsequently support and/or manipulate a portion of a human below a knee of the human. The respective outer shells of the various versions differ generally according to the size and shape of the inner shells to further the support and/or manipulation of targeted portions of the human. As depicted, in some instances the same outer shell can be used for different applications using differently extended inner shells as further discussed below.

Figure 22:
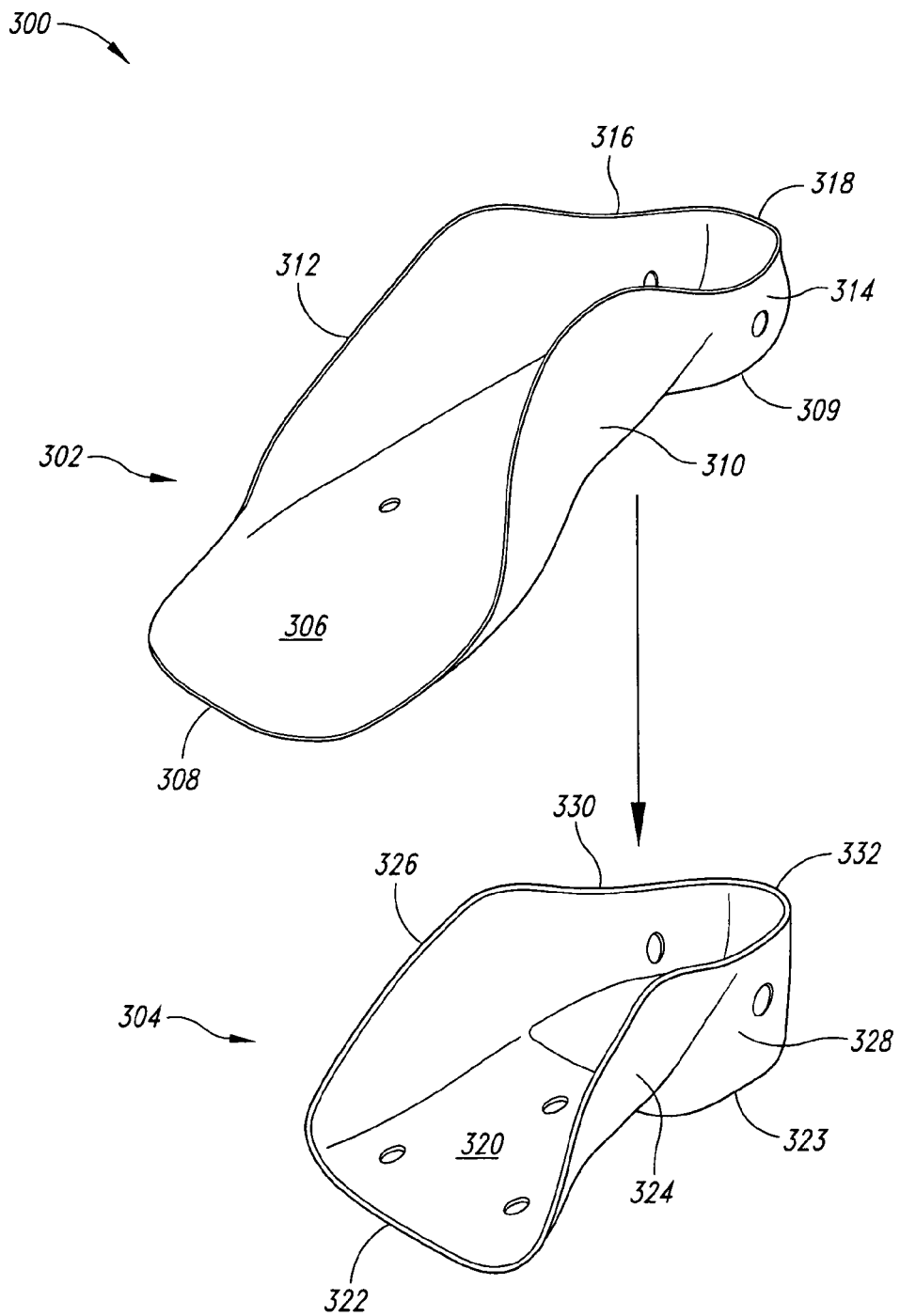
FIG. 22 is an exploded isometric view of a short height orthotic support device implementation showing inner and outer shells separated.
Figure 23:
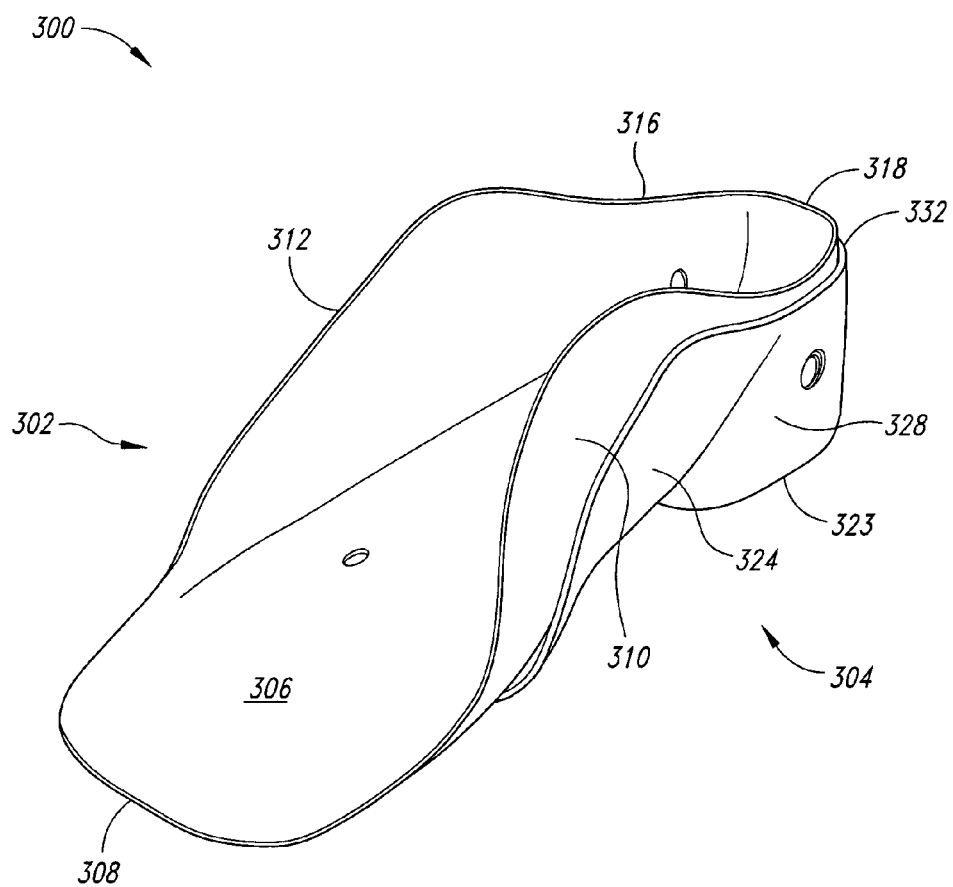
FIG. 23 is an isometric view of the short height orthotic device implementation of FIG. 22 showing the inner and outer shells coupled together.
Figure 24:
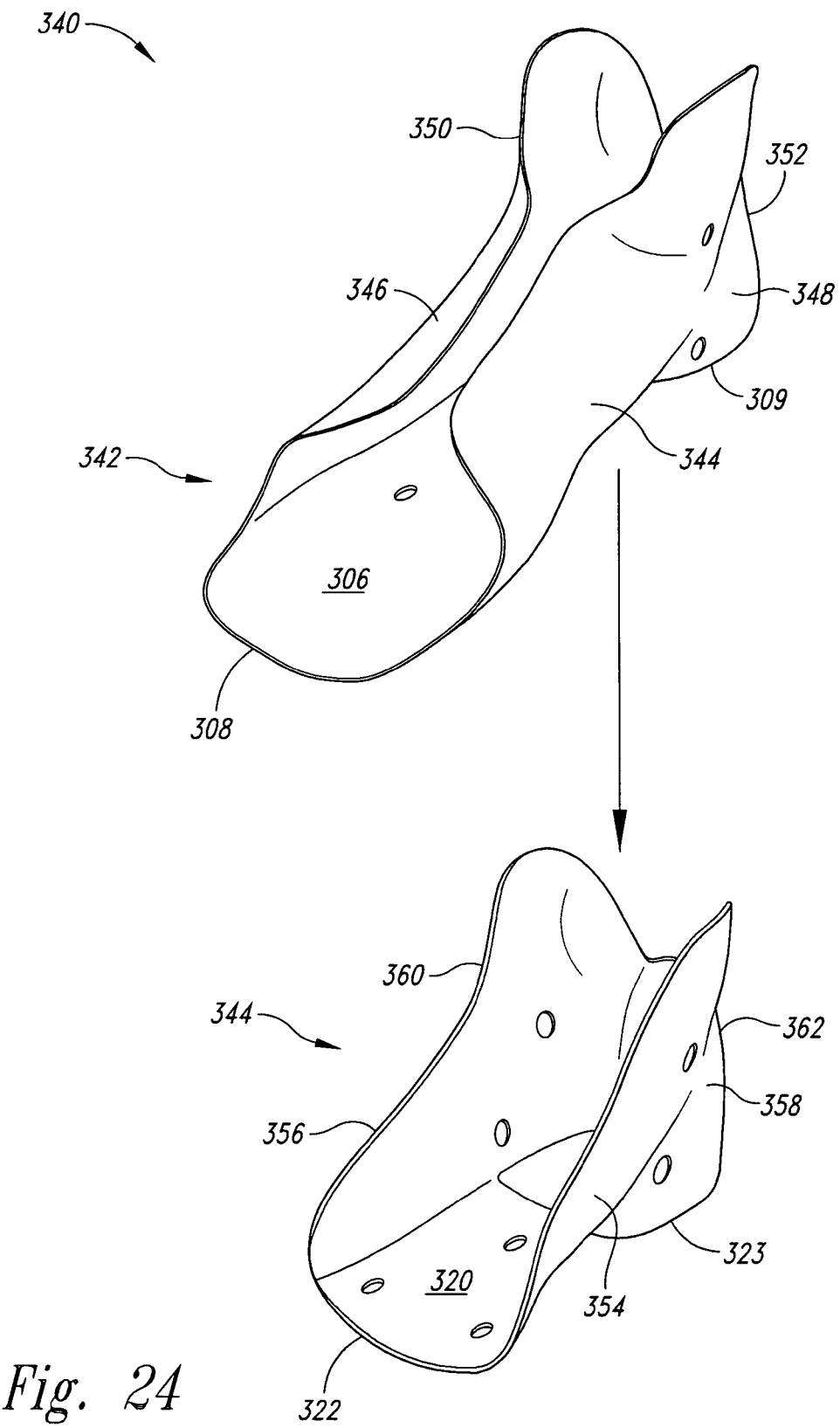
FIG. 24 is an exploded isometric view of a medium height orthotic support device implementation showing inner and outer shells separated.
Figure 25:
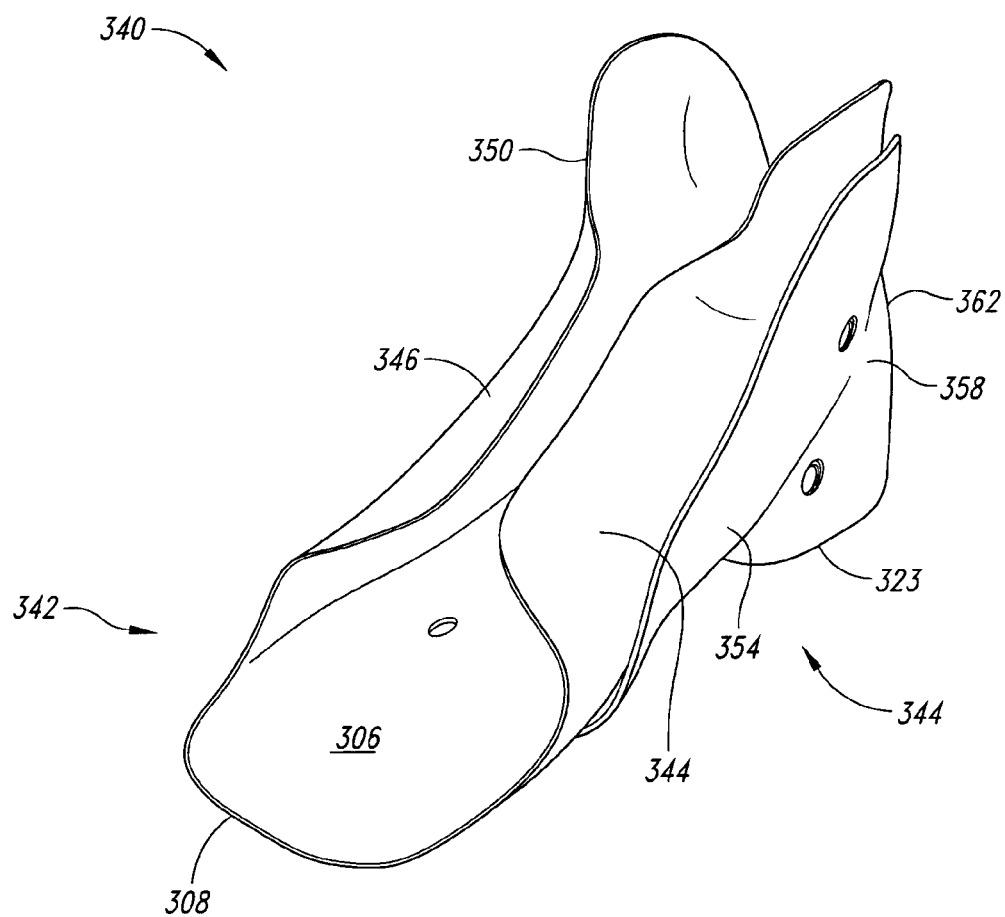
FIG. 25 is an isometric view of the medium height orthotic device implementation of FIG. 24 showing the inner and outer shells coupled together.

For instance, a short height orthotic support device implementation 300 is shown in FIGS. 22 and 23 as having an inner shell 302 and an outer shell 304. As explained above, the inner shell 302 and the outer shell 304 can be made from substantially the same material, similar material or even different material with substantially the same, similar, or even varying thicknesses whereby the inner shell 302 and the outer shell 304 can have similar compressibility characteristics, but may have varying rigidity and flexibility characteristics to accomplish an overall targeted balance of a desired degree of orthotic support and/or manipulation and an acceptable user comfort level. The short height orthotic device 300 shown is constructed to be worn on a right foot of a human. A similar but mirrored depiction would be applicable for a left foot of a human. The inner shell 302 includes a base portion 306 with an anterior portion 308 and a heel portion 309. In other implementations the anterior portion 308 can be adjusted to extend either more or less forward than depicted in FIG. 22. The heel portion 309 is shaped to conform with a heel of a human foot to provide desired orthotic support and/or manipulation while maintaining an acceptable level of user comfort given the material selection and thicknesses involved. The inner shell 302 further includes an anterior medial wall portion 310, an anterior lateral wall portion 312, a posterior medial wall portion 314, a posterior lateral wall portion 316, and a posterior wall portion 318, which are shaped and extended to provide orthotic support and/or manipulation to a lower region of a human foot which can include but not be limited to such regions as hindfoot regions, arch regions, navicular regions, metatarsal regions, sesamoid regions, among other regions. The short height orthotic support device implementation 300 shown has the upward extent of both the inner shell 302 and the outer shell 304 terminating below the talocrural joint (ankle joint) of the foot of the human wearer.

The outer shell 304 combines with the inner shell 302 to provide desired orthotic support, manipulation, and user comfort levels. The outer shell 304 includes a base portion 320 with an anterior portion 322 and a heel portion 323. In other implementations the anterior portion 322 can be adjusted to extend either further or less forward than depicted in FIG. 22 according to the degree of extension of the anterior portion 308 of the inner shell 302. The heel portion 323 provides a raised shoe-like heel to provide desired orthotic support and/or manipulation while maintaining an acceptable level of user comfort given the material selection and thicknesses involved. In other implementations, the heel portion 323 can be more or less emphasized than that depicted in FIG. 22 based upon desired orthotic support, manipulation, and user comfort levels. The outer shell 304 further includes an anterior medial wall portion 324, an anterior lateral wall portion 326, a posterior medial wall portion 328, a posterior lateral wall portion 330, and a posterior wall portion 332, which are shaped and extended to provide orthotic support and/or manipulation and desired user comfort levels in combination with the inner shell 302.

A medium height orthotic support device implementation 340 is shown in FIGS. 24-29 as having an inner shell 342 and an outer shell 344. As explained above, the inner shell 342 and the outer shell 344 can be made from substantially the same material, similar material or even different material with substantially the same, similar, or even varying thicknesses whereby the inner shell 342 and the outer shell 344 can have similar compressibility characteristics, but may have varying rigidity and flexibility characteristics to accomplish an overall targeted balance of a desired degree of orthotic support and/or manipulation and an acceptable user comfort level. The medium height orthotic device 340 shown is constructed to be worn on a right foot of a human. A similar but mirrored depiction would be applicable for a left foot of a human.

The inner shell 342 includes the base portion 306 with the anterior portion 308 and the heel portion 309. In other implementations the anterior portion 308 can be adjusted to extend either more or less forward than depicted in FIG. 24. The inner shell 342 further includes an anterior medial wall portion 344, an anterior lateral wall portion 346, a posterior medial wall portion 348, a posterior lateral wall portion 350, and a posterior wall portion 352, which are shaped and extended farther than corresponding regions of the inner shell 302 of the short height orthotic device 300 to provide orthotic support and/or manipulation to a human foot and additional regions and can include those regions mentioned above for the short height orthotic device and also can include but not be limited to such regions as malleolus regions and talocrural regions.

The outer shell 344 combines with the inner shell 342 to provide desired orthotic support, manipulation, and user comfort levels. The outer shell 344 includes the base portion 320 with the anterior portion 322 and the heel portion 323. In other implementations the anterior portion 308 can be adjusted to extend either more or less forward than depicted in FIG. 24 according to the degree of extension of the anterior portion 308 of the inner shell 302. The heel portion 323 provides a raised shoe-like heel to provide desired orthotic support and/or manipulation while maintaining an acceptable level of user comfort given the material selection and thicknesses involved. In other implementations, the heel portion 323 can be more or less emphasized than that depicted in FIG. 24 based upon desired orthotic support, manipulation, and user comfort levels. The outer shell 344 further includes an anterior medial wall portion 354, an anterior lateral wall portion 356, a posterior medial wall portion 358, a posterior lateral wall portion 360, and a posterior wall portion 362, which are shaped and extended to provide orthotic support and/or manipulation in combination with the inner shell 342.

Figure 26:
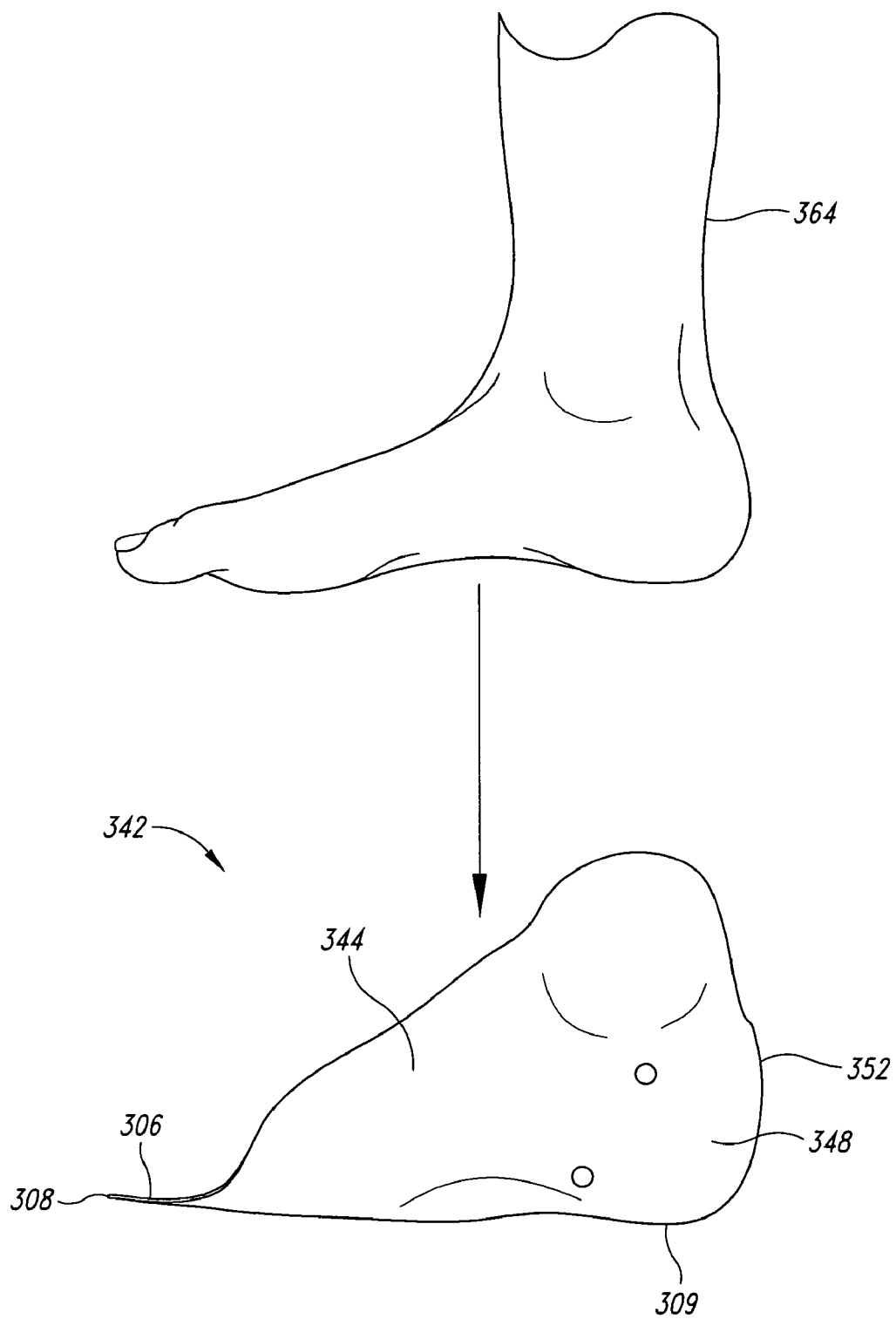
FIG. 26 is a side elevational view showing insertion of a human foot into the inner shell of the medium height orthotic device implementation of FIG. 24 forming a foot-inner shell combination.
Figure 27:
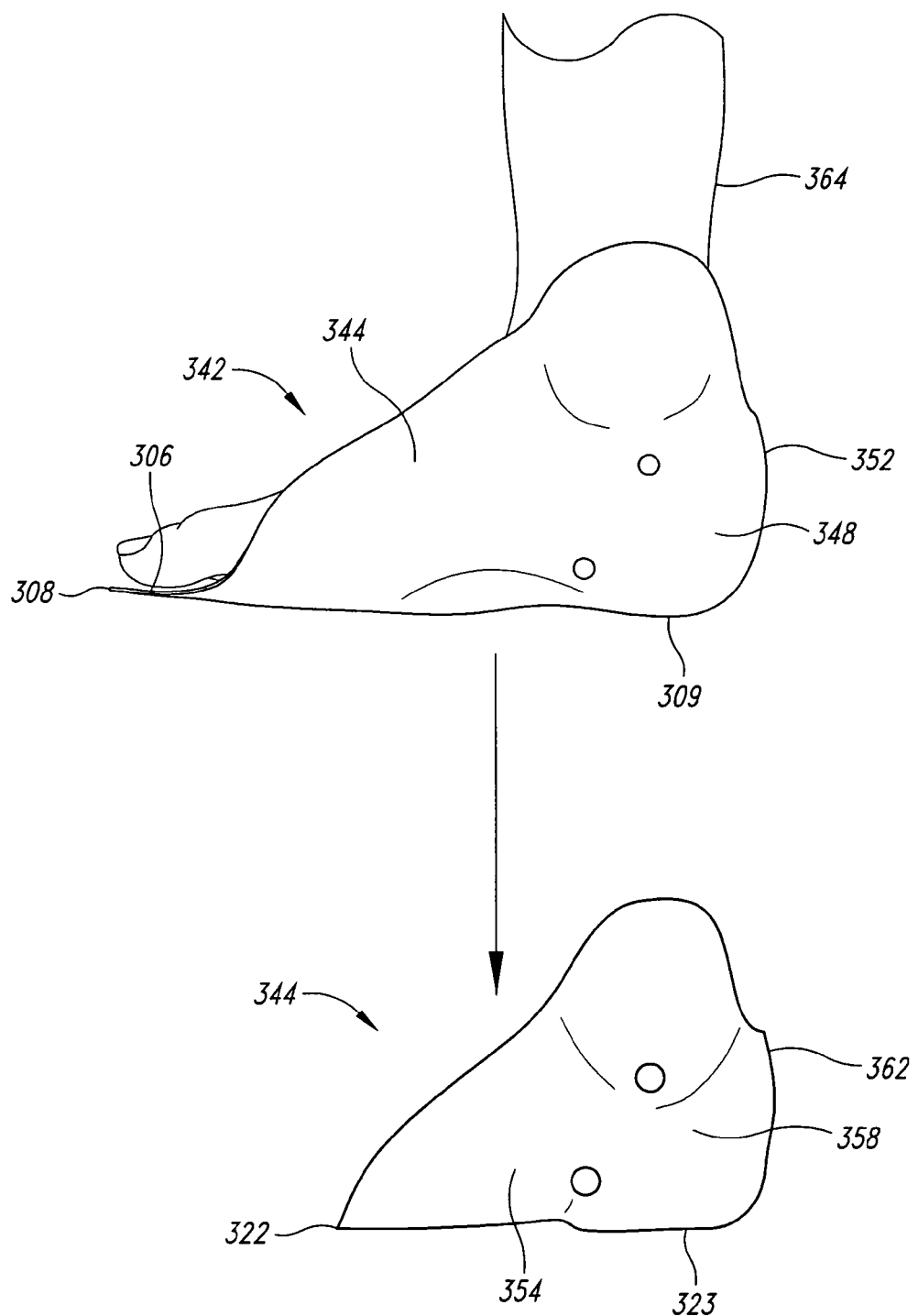
FIG. 27 is a side elevational view showing insertion of the foot-inner shell combination into the outer shell of the medium height orthotic device implementation of FIG. 24 forming a foot-device combination.
Figure 28:
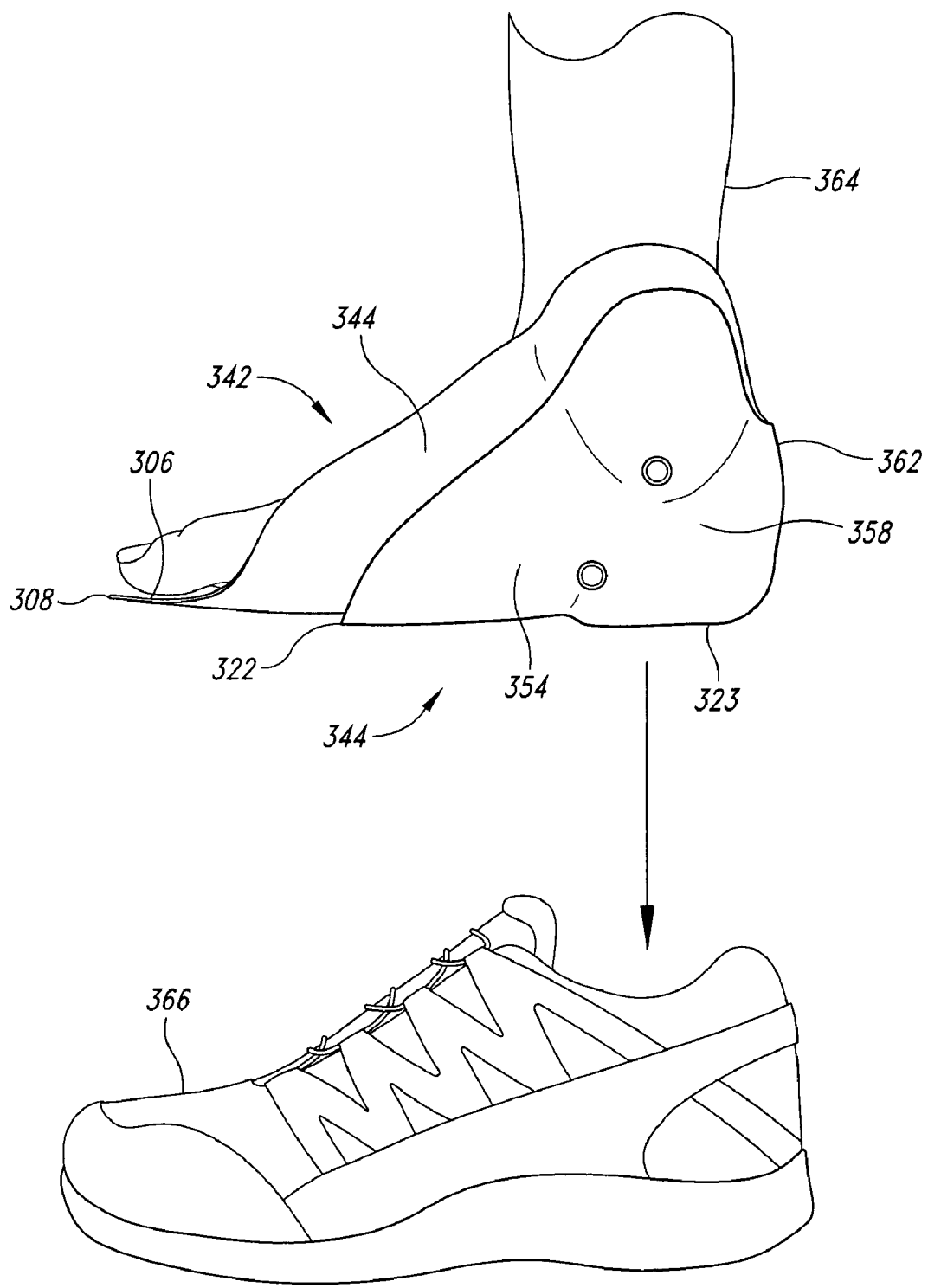
FIG. 28 is a side elevational view showing insertion of the foot-device combination of the medium height orthotic device implementation of FIG. 24 into an exemplary footwear.
Figure 29:
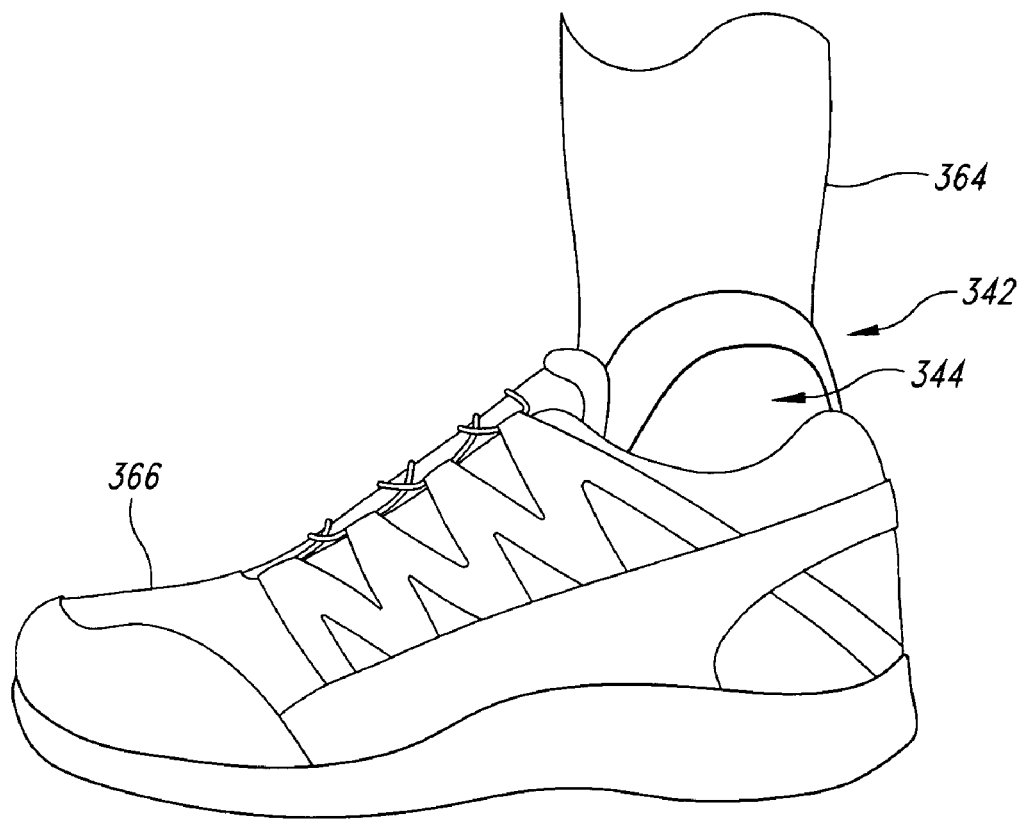
FIG. 29 is a side elevational view showing the foot-device combination of the medium height orthotic device implementation of FIG. 24 inserted into the exemplary footwear.

A portion of a human 364 is depicted in FIG. 26 as being aligned for insertion with the inner shell 342 of the medium height orthotic device 340. The portion of the human 364 is shown in FIG. 27 as having been inserted in the inner shell 342 and in alignment for insertion into the outer shell 344. The inner shell 342 having received the portion of the human 364 is shown in FIG. 28 as having been inserted into the outer shell 344 and in alignment for insertion into an exemplary footwear 366. The medium height orthotic support device implementation 340 shown has the upward extent of both the inner shell 342 and the outer shell 344 terminating immediately above the talocrural joint of the foot of the human wearer, and below the calf of the wearer. The outer shell 344, having received the inner shell 342 which received the portion of the human 264, is shown in FIG. 29 as having been inserted in the exemplary footwear 366.

Figure 30:
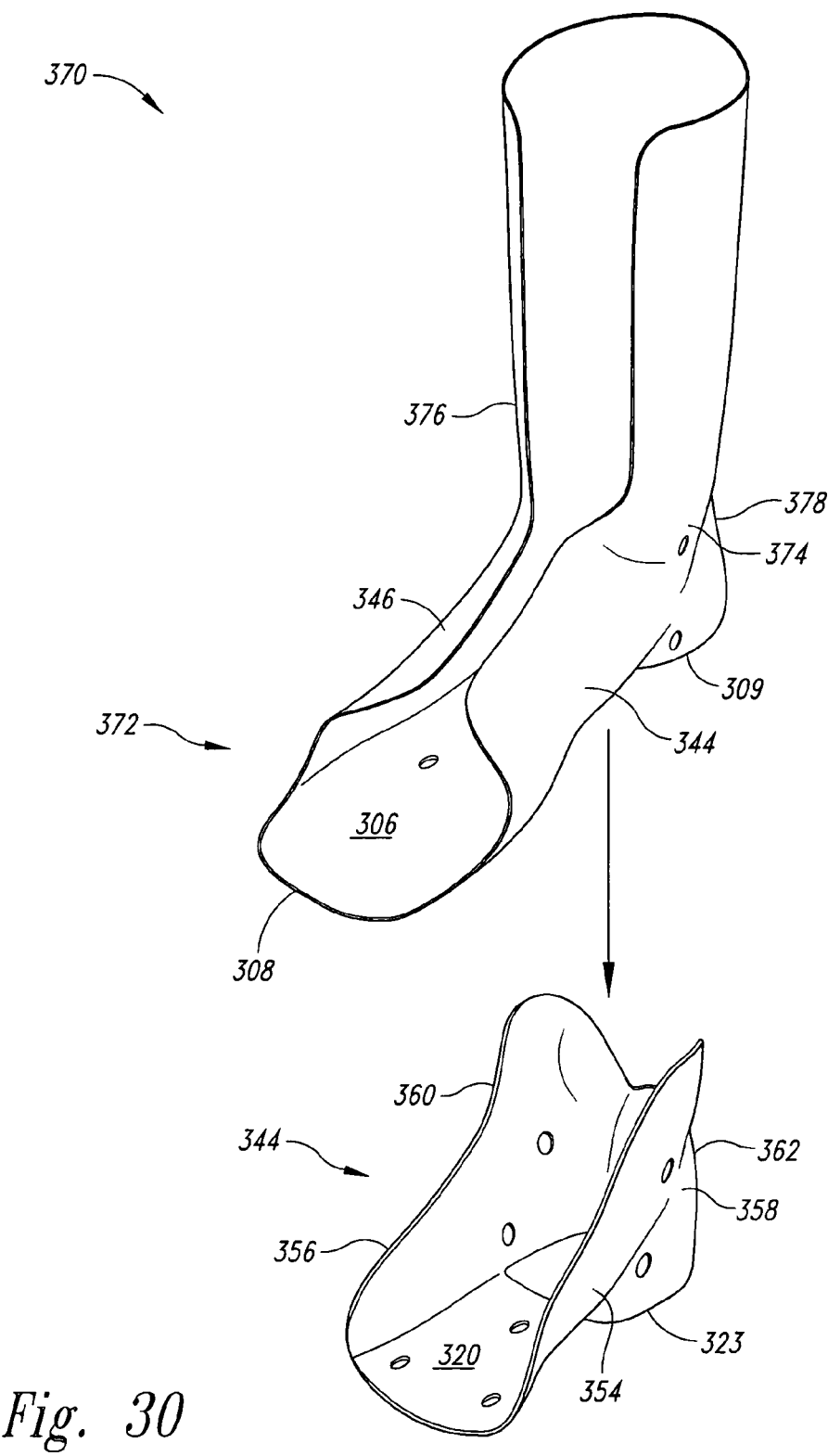
FIG. 30 is an exploded isometric view of a tall height orthotic support device implementation showing inner and outer shells separated.
Figure 31:
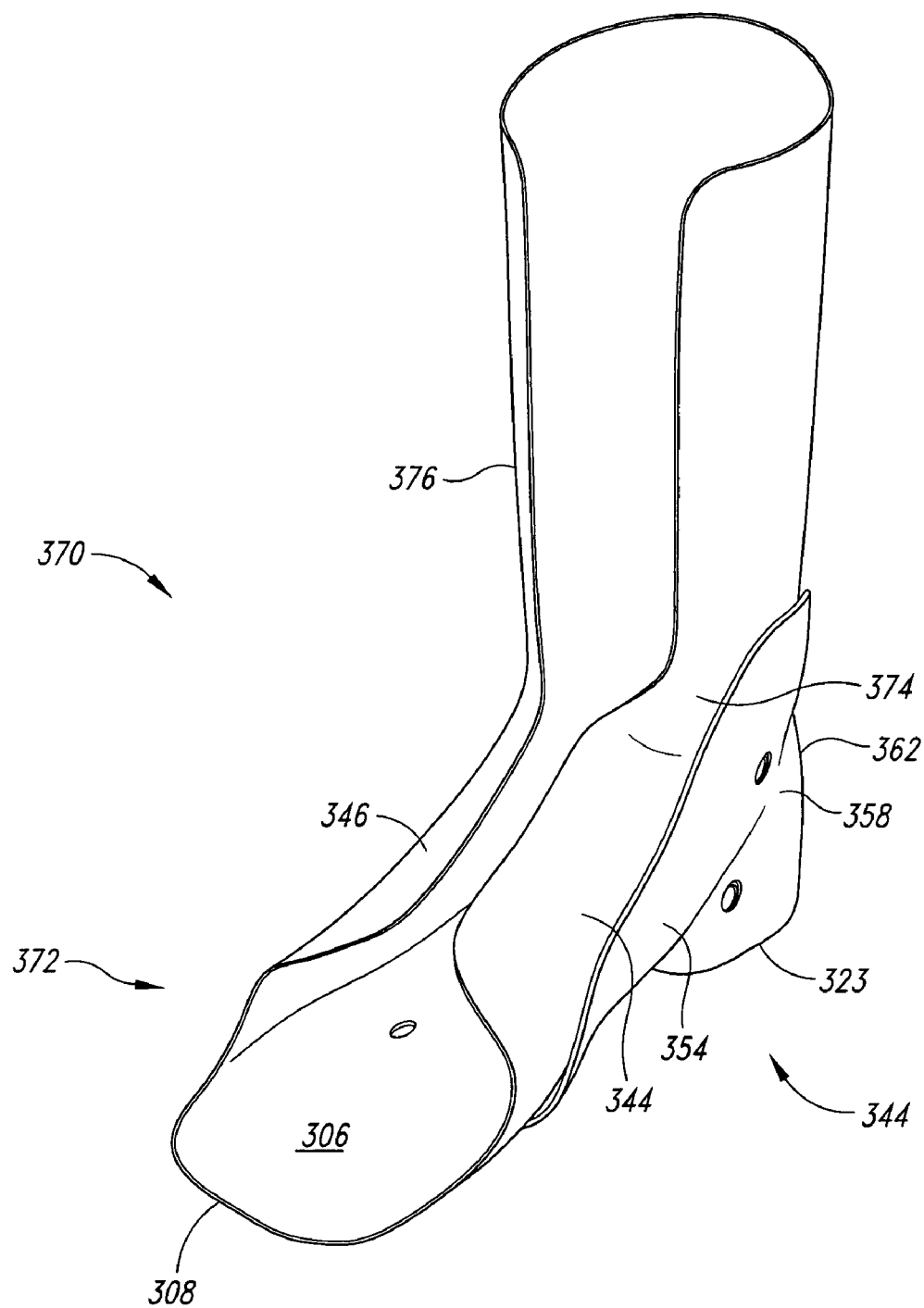
FIG. 31 is an isometric view of the tall height orthotic device implementation of FIG. 30 showing the inner and outer shells coupled together.

A tall height orthotic support device implementation 370 is shown in FIGS. 30 and 31 as having an inner shell 372 and the outer shell 344. As explained above, the inner shell 372 and the outer shell 344 can be made from substantially the same material, similar material or even different material with substantially the same, similar, or even varying thicknesses whereby the inner shell 372 and the outer shell 344 can have similar compressibility characteristics, but may have varying rigidity and flexibility characteristics to accomplish an overall targeted balance of a desired degree of orthotic support and/or manipulation and an acceptable user comfort level. The tall height orthotic device 370 shown is constructed to be worn on a right foot of a human. A similar but mirrored depiction would be applicable for a left foot of a human.

The inner shell 372 includes the base portion 306 with the anterior portion 308 and the heel portion 309. In other implementations the anterior portion 308 can be adjusted to extend either more or less forward than depicted in FIG. 30. The inner shell 372 further includes the anterior medial wall portion 344, the anterior lateral wall portion 346, a posterior medial wall portion 374, a posterior lateral wall portion 376, and a posterior wall portion 378, which are shaped and extended farther than corresponding regions of the inner shell 342 of the medium height orthotic device 340 to provide orthotic support and/or manipulation to a human foot and additional regions of a human and can include those regions mentioned above for the medium height orthotic device and also can include but not be limited to such regions of the human superior to what the medium height orthotic device may influence. The tall height orthotic support device implementation 370 shown has the upper extent of both the inner shell 372 and the outer shell 344 terminating above the talocrural joint of the foot of the human wearer, with the outer shell 344 terminating just above the talocrural joint and the inner shell 372 extending substantially higher to about the mid-calf area of the human wearer.

While the present invention is illustrated by description of several embodiments and while the illustrative embodiments are described in detail, it is not the intention of the applicants to restrict or in any way limit the scope of the appended claims to such detail. Additional advantages and modifications within the scope of the appended claims will readily appear to those sufficed in the art. The invention in its broader aspects is therefore not limited to the specific details, representative apparatus and methods, and illustrative examples shown and described. Accordingly, departures may be made from such details without departing from the spirit or scope of applicant's general concept.

The invention claimed is:

1. A corrective device wearable on a portion of a human below a knee of the human including at least a portion of the human's foot and to be positioned inside of a footwear while on the portion of the human, the portion of the human having at least a misalignment, the corrective device comprising:

an inner shell having a first material composition with a first rigidity selected to have sufficient rigidity to move and hold the foot in a corrected position to prevent abduction of the foot when the foot pronates, the inner shell shaped to accommodate receiving the portion of the human into the inner shell to supportingly couple with the portion of the human, the inner shell being a continuous contoured form without articulation joints or selectable adjustments during use, and having a base portion extending below the foot of the human and a heel portion shaped to conform to the heel of the human and provide at least one of orthotic support and manipulation thereto, the inner shell further including a posterior wall portion extending from the heel portion thereof upward above and fully covering the heel of the human; and an outer shell having a second material composition with a second rigidity selected to control the biomechanical positioning and alignment of the portion of the human, the second material composition being substantially the same as the first material composition, the inner and outer shells being separable portions of the corrective device and not secured together, the outer shell shaped to accommodate removably receiving the inner shell into the outer shell to provide in combination with the inner shell a cumulative corrective support greater than provided by either the inner shell or the outer shell by itself, and to accommodate positioning into the footwear for coupling with the footwear, the outer shell being a continuous contoured form without articulation joints or selectable adjustments during use, and having a base portion extending below the base portion of the inner shell and a heel portion shaped to provide a raised heel to provide at least one of orthotic support and manipulation to the heel of the human, the outer shell further including a posterior wall portion extending from the heel portion thereof upward above and fully covering the heel of the human, the inner shell and the outer shell being configured for insertion of the inner shell with the portion of the human therein into the outer shell to form a support assembly insertable into the footwear for wear by the human within the footwear and for removal of the inner shell with the portion of the human therein from within the outer shell for subsequent removal of the portion of the human from the inner shell, the inner shell and the outer shell being sized and shaped such that when the inner shell is coupled with the portion of the human and the inner shell is within the outer shell and the outer shell is positioned in the footwear, at least a portion of a pressure is distributed by the outer shell and the inner shell to the portion of the human to provide correction to the misalignment of the portion of the human, whereby the human can wear the inner shell inside of the outer shell inside of the footwear in comfort while the portion of the pressure is being applied to facilitate correction of the misalignment.

2. The corrective device of claim 1 wherein the inner shell and the outer shell have substantially the same thickness, the inner shell having an inner shell support wall with a upwardly opening elongated gap having a width smaller than the width of the foot, the inner shell support wall being sufficiently flexibility to permit selected temporary expansion thereof for passage of the foot through the inner shell support wall gap, the inner shell support wall extending away from the inner shell support wall gap being formed as an uninterrupted separate first unit, and the outer shell having an outer shell support wall with a upwardly opening elongated gap having a width smaller than the foot, the outer shell support wall being sufficiently flexibility to permit selected temporary expansion thereof for passage of the foot with the inner shell thereon through the outer shell support wall gap, the outer shell support wall extending away from the outer shell support wall gap being formed as an uninterrupted separate second unit.

3. The corrective device of claim 1 wherein the inner shell and the outer shell each have portions with different thicknesses, the inner shell having an inner shell support wall with a upwardly opening elongated gap having a width smaller than the width of the foot, the inner shell support wall being sufficiently flexibility to permit selected temporary expansion thereof for passage of the foot through the inner shell support wall gap, the inner shell support wall extending away from the inner shell support wall gap being formed as an uninterrupted separate first unit and the outer shell having an outer shell support wall with a upwardly opening elongated gap having a width smaller than the foot, the outer shell support wall being sufficiently flexibility to permit selected temporary expansion thereof for passage of the foot with the inner shell thereon through the outer shell support wall gap, the outer shell support wall extending away from the outer shell support wall gap being formed as an uninterrupted separate second unit.

4. The corrective device of claim 1 wherein the first material composition of the inner shell and the second material composition of the outer shell includes at least one of the following: a plastic, a vinyl, a composite, an ethylene, and a polymer.

5. The correct of device of claim 1 wherein the inner shell and the outer shell have an upper extent terminating below the talocrural joint of the portion of the human.

6. The correct of device of claim 1 wherein the inner shell and the outer shell have an upper extent terminating above the talocrural joint of the portion of the human, below the calf of the human.

7. The correct of device of claim 1 wherein the inner shell and the outer shell have an upper extent terminating above the talocrural joint of the portion of the human, with the inner shell extending upward above the outer shell to a mid-calf area of the human, the inner shell above the talocrural joint having a continuous contoured form and having no articulation joints to inhibit rearward rearward flexing during use.

8. The corrective device of claim 1 wherein the inner shell and the outer shell when the inner shell is within the outer shell provide a preset raised arch region and depressions.

9. The corrective device of claim 8 for the portion of the body having at least a foot region further including a preset form of features to in part compensate for prominent features of the foot.

10. The corrective device of claim 8 further including a preset form of features to in part establish a neutral biomechanical set form.

11. The corrective device of claim 1 for the portion of the human including a foot region and a heel region wherein the outer shell and inner shell are shaped such that the pressure distribution by the outer shell and the inner shell imparts a force on a distal region of the foot region and is distributed longitudinally rearwardly to the heel region.

12. The corrective device of claim 1 wherein the inner shell has a thickness between 0.0625 inches and 0.09 inches.

13. The corrective device of claim 1 wherein support portions of the inner shell have a thickness of between 0.5 millimeters and 3 millimeters, and wherein support portions of the outer shell have a thickness of between 0.5 millimeters and 3 millimeters.

14. The corrective device of claim 1 wherein the inner shell and the outer shell in combination provide a perimeter region with an amount of flexibility allowing deflection inward or outward by more than a millimeter.

15. The corrective device of claim 1 wherein the outer shell and the inner shell in combination when the inner shell is within the outer shell form a lower semi-rigid fitting module and an upper semi-rigid fitting module.

16. The corrective device of claim 1 wherein the inner shell and the outer shell are made from a polyethylene based plastic.

17. The corrective device of claim 1 wherein the outer shell upwardly terminates in a rearward upper perimeter ridge region and the inner shell upwardly terminates in a perimeter ridge, when the inner shell is positioned within the outer shell the perimeter ridge of the inner shell is positioned above the rearward upper perimeter ridge region of the outer shell such that the inner and outer shell upwardly terminate at different locations to provide a blending of pressures from the perimeter ridge of the inner shell and the rearward upper perimeter ridge region of the outer shell to lessen edge pressure applied to the portion of the human.

18. The corrective device of claim 17 wherein the inner shell includes an anterior portion and the outer shell includes an anterior portion, with the anterior portion of the inner shell extending forward of the anterior portion of the outer shell.

19. The corrective device of claim 18 wherein the inner shell includes an anterior lateral wall portion and an anterior medial wall portion, with the anterior portion of the inner shell forwardly terminating forward of the anterior lateral and anterior medial wall portions to provide a region of increased flexibility of the corrective device at which the metatarsal heads of the human's foot end and the human's foot can pivot during walking or running.

20. The corrective device of claim 1 wherein the inner shell and outer shell are shaped to provide orthotic sensory feedback to provide the human with a heightened sense of foot portion position to aid in proper alignment of the foot portion to contribute to the correction of the misalignment.

21. The corrective device of claim 1 wherein the first and second material compositions are selected to provide flexibility of the inner shell and the outer shell allowing day-long wear by the human.

22. The corrective device of claim 1 wherein the inner shell and the outer shell are sized and shaped to allow for the pressure to be distributed without allowing the foot portion to completely collapse.

23. The corrective device of claim 1 wherein the outer support shell includes a heel cup region in a rearward portion of the outer support shell and the inner shell includes a portion to engage with the heel cup region.

24. The corrective device of claim 1 wherein the inner shell is receivable within the outer shell to accommodate bio-structural variations of the portion of the human.

25. The corrective device of claim 1 wherein the outer shell has a central slit region and the inner shell has a central slit region.

26. The corrective device of claim 1 wherein the outer shell and the inner shell are at least in part plastic.

27. The corrective device of claim 1 to be worn on the portion of a human including a heel region, wherein the inner shell and the outer shell are sized and shaped such that the amount of correction to the misalignment by the pressure distributed by the rigidity of the outer shell and the rigidity of the inner shell aligns the heel region into a substantially vertical position.

28. The corrective device of claim 1 wherein the inner shell and the outer shell are shaped such that the amount of correction to the misalignment by the pressure distributed by the rigidity of the outer shell and the rigidity of the inner shell maintains medial and lateral alignment of the portion of the human.

29. The corrective device of claim 1 to be worn on the portion of a human including a forefoot region, wherein the inner shell and the outer shell are shaped such that the amount of correction to the misalignment by the pressure distributed by the rigidity of the outer shell and the rigidity of the inner shell aligns the forefoot region into a neutral position.

30. The corrective device of claim 1 wherein the first material composition and the second material composition have a rigidity such that the inner and outer shells distribute a portion of the pressure upon regions adjacent to the misalignment.

31. The corrective device of claim 1 wherein the outer shell includes a perimeter support region having medial and lateral sections.

32. The corrective device of claim 1 wherein the outer shell has an interior chamber region with an inner surface and the inner shell has an exterior surface configured to engage with the inner surface.

33. The corrective device of claim 1 to be worn on the portion of a human including a heel region, wherein the inner shell and the outer shell are shaped such that the amount of correction to the misalignment by the pressure distributed by the rigidity of the outer shell and the rigidity of the inner shell aligns the heel in a rearward proximal location of the corrective device.

34. The corrective device of claim 1 wherein the outer shell has a lateral region and the inner shell has an extension region that extends longitudinally forward from the lateral region of the outer shell.

35. The corrective device of claim 1 wherein the outer shell has a lateral region with a base region and the inner shell has an extension region, the base region configured to support the extension region to control abduction.

36. The corrective device of claim 1 wherein the inner shell has an extension region extending forward beyond the outer shell and the rigidity of the inner shell in the extension region has flexibility allowing bending of the inner shell in the extension region as the human walks or runs.

37. The corrective device of claim 1 wherein the inner shell is substantially incompressible under the weight of the human during use of the corrective device.

38. The corrective device of claim 1 wherein the outer shell and the inner shell in combination provide a base region, a forward region, and an upper region that includes a perimeter ridge.

39. The corrective device of claim 1 wherein the inner shell and the outer shell are shaped such that the amount of correction to the misalignment by the pressure distributed by the rigidity of the outer shell and the rigidity of the inner shell aligns the foot region into a biomechanical neutral position.

40. The corrective device of claim 1 wherein the inner shell and the outer shell in combination provide a raised medial arch region.

41. The corrective device of claim 1 for the portion of the human having the misalignment include at least one of a pronation, a supination, and a varus-vulgus condition, wherein the inner shell and the outer shell are shaped to distribute the pressure for correcting the misalignment.

42. The corrective device of claim 1 for the portion of the human having the misalignment include at least a pronation condition involving at least one of eversion, arch movement to flat position, and abduction, wherein the inner shell and the outer shell are shaped to distribute the pressure for correcting the pronation condition.

43. The corrective device of claim 1 to be worn on the portion of a human including an ankle portion and a lower foot region, wherein the inner shell is shaped to accommodate receiving at least a portion of the ankle and the lower foot region into the inner shell.

44. A strapless corrective device to be worn on at least a portion of a foot of a human and to be positioned inside of a footwear while on the foot, the portion of the foot at least having a misalignment, the corrective device comprising:

an inner shell and an outer shell, the inner shell having an inner shell support wall with a upwardly opening elongated gap having a width smaller than the width of the foot, the inner shell support wall being sufficiently flexibility to permit selected temporary expansion thereof for passage of the foot through the inner shell support wall pap, the inner shell support wall extending away from the inner shell support wall gap being formed as an uninterrupted separate first unit having a continuous contoured form without articulation joints or selectable adjustments during use, and the outer shell having an outer shell support wall with a upwardly opening elongated gap having a width smaller than the foot, the outer shell support wall being sufficiently flexibility to permit selected temporary expansion thereof for passage of the foot with the inner shell thereon through the outer shell support wall gap, the outer shell support wall extending away from the outer shell support wall gap being formed as an uninterrupted separate second unit having a continuous contoured form without articulation joints or selectable adjustments during use, the inner shell shaped to accommodate receiving therein and supportingly couple with the portion of the foot, the inner shell having a shape and first rigidity applying a pressure to the portion of the foot to in part control the biomechanical positioning and alignment of the portion of the foot, and the outer shell shaped to accommodate removably receiving therein the inner shell with the portion of the foot therein, and allow positioning into the footwear, the outer shell having a second rigidity applying a pressure to the portion of the foot to in part control the biomechanical positioning and alignment of the portion of the foot, the first rigidity and second rigidity being substantially the same, the inner and outer shells being separable portions of the corrective device unsecured to each other and disconnectable from each other when not in use yet when the inner shell is within the outer shell during use jointly providing pressure to the portion of the foot for correction of the misalignment of the portion of the foot through only the support provided to the portion of the foot resulting from their rigidity without use of straps, the inner shell and the outer shell being sized and shaped such that when the inner shell is coupled with the portion of the human and the inner shell is within the outer shell and the outer shell is positioned in the footwear, at least a portion of the pressure is distributed by the outer shell and the inner shell over a desired area of the portion of the foot providing an amount of correction to the misalignment of the portion of the foot while allowing the human to wear the inner shell inside of the outer shell inside of the footwear.

45. A method for use with a portion of a human below a knee of the human and a footwear, the portion of the human having at least a misalignment, the method comprising:

providing an inner shell having a first material composition with a first rigidity and shape to accommodate receiving the portion of the human into the inner shell to supportingly couple with the portion of the human and provide support thereto the first rigidity being sufficient for the inner shell to move and hold the foot in a corrected position to prevent abduction of the foot when the foot pronates, the inner shell being a continuous contoured form without articulation joints or selectable adjustments during use;

providing an outer shell having a second material composition substantially the same as a first and material composition and with a second rigidity and shape to accommodate removably receiving the inner shell into the outer shell to provide in combination with the inner shell a cumulative corrective support greater than provided by either the inner shell or the outer shell by itself and to control the biomechanical positioning and alignment of the portion of the human, the inner and outer shells being separable portions of the corrective device and not secured together, and disconnectable from each other when not in use, the outer shell being a continuous contoured form without articulation joints or selectable adjustments during use, the outer shell further shaped to accommodate positioning into the footwear for coupling with the footwear;

first, receiving the portion of the human into the inner shell to supportingly couple with the portion of the human;

second, receiving the inner shell with the portion of the human already therein into the outer shell to form a support assembly without securing the inner and outer shells together and with the inner and outer shells being readily disconnectable from each other when not in use;

third, positioning the outer shell into the footwear while the inner shell is positioned within the outer shell and the inner shell is coupled with the portion of the human; and distributing a pressure caused by the combined first rigidity of the inner shell and the second rigidity of the outer shell to the portion of the human to move and hold the foot in the corrected position and provide an amount of correction to the misalignment of the portion of the human while the human wears the inner shell inside of the outer shell inside of the footwear.

46. A corrective device for a portion of a human below a knee of the human including at least a portion of the human's foot, the portion of the human having at least a misalignment, the corrective device comprising:

first means for receiving the portion of the human and applying a pressure to the portion of the foot to move and hold the foot in a corrected position and thereby in part control the biomechanical positioning and alignment of the portion of the foot to prevent abduction of the foot when the foot pronates; and second means for receiving the first means therein and coupling with a footwear and applying a pressure to the portion of the foot to in part control the biomechanical positioning and alignment of the portion of the foot, the first and second means being unsecured to each other and disconnectable from each other when not in use yet when the first means is within the second means during use jointly providing pressure to the portion of the foot for correction of the misalignment of the portion of the foot without use of straps.

47. A corrective device wearable on a portion of a human below a knee of the human including at least a portion of the human's foot and to be positioned inside of a footwear while on the portion of the human, the portion of the human having at least a misalignment, the corrective device comprising:

an inner shell and an outer shell, the inner shell having an inner shell support wall with a upwardly opening elongated gap having a width smaller than the width of the foot, the inner shell support wall being sufficiently flexibility to permit selected temporary expansion thereof for passage of the foot through the inner shell support wall gap, the inner shell support wall extending away from the inner shell support wall gap being formed as an uninterrupted separate first unit having a continuous contoured form without articulation joints or selectable adjustments during use, and the outer shell having an outer shell support wall with a upwardly opening elongated gap having a width smaller than the foot, the outer shell support wall being sufficiently flexibility to permit selected temporary expansion thereof for passage of the foot with the inner shell thereon through the outer shell support wall gap, the outer shell support wall extending away from the outer shell support wall gap being formed as an uninterrupted separate second unit having a continuous contoured form without articulation joints or selectable adjustments during use, the inner shell shaped to accommodate receiving therein and supportingly couple with the portion of the foot, the inner shell having a shape and first rigidity sufficient to move and hold the foot in a corrected position by applying a pressure to the portion of the foot to in part control the biomechanical positioning and alignment of the portion of the foot, and having a base portion extending below the foot of the human and a heel portion shaped to conform to the heel of the human and provide at least one of orthotic support and manipulation thereto, the inner shell further including a posterior wall portion extending from the heel portion thereof upward above and fully covering the heel of the human, and the outer shell shaped to accommodate removably receiving therein the inner shell with the portion of the foot therein and allow positioning into the footwear, the outer shell having a second rigidity to apply a pressure to the portion of the foot to in part control the biomechanical positioning and alignment of the portion of the foot, and having a base portion extending below the base portion of the inner shell and a heel portion shaped to provide a raised heel to provide at least one of orthotic support and manipulation to the heel of the human, the outer shell further including a posterior wall portion extending from the heel portion thereof upward above and fully covering the heel of the human, the first rigidity and second rigidity providing in combination a cumulative corrective support greater than provided by either the inner shell or the outer shell by itself, the inner and outer shells being separable portions of the corrective device unsecured to each other and disconnectable from each other when not in use yet when the inner shell is within the outer shell during use jointly providing pressure to the portion of the foot for correction of the misalignment of the portion of the foot through only the support provided to the portion of the foot resulting from their rigidity without use of straps, the inner shell and the outer shell being sized and shaped such that when the inner shell is coupled with the portion of the human and the inner shell is within the outer shell and the outer shell is positioned in the footwear, at least a portion of the pressure is distributed by the outer shell and the inner shell over a desired area of the portion of the foot to provide an amount of correction to the misalignment of the portion of the foot while allowing the human to wear the inner shell inside of the outer shell inside of the footwear.

48. A strapless corrective device wearable on a portion of a human below a knee of the human including at least a portion of the human's foot and to be positioned inside of a footwear while on the portion of the human, the portion of the human having at least a misalignment, the corrective device comprising:

an inner shell shaped to accommodate receiving the portion of the human therein and supportingly couple with the portion of the human, the inner shell having a first rigidity to move and hold the foot in a corrected position by applying a pressure the portion of the human therein within the inner shell to prevent abduction of the foot when the foot pronates, the inner shell being a continuous contoured form without articulation joints or selectable adjustments during use; and an outer shell shaped to accommodate removably receiving the inner shell with the portion of the human therein into the outer shell, the outer shell having a second rigidity controlling the biomechanical positioning and alignment of the portion of the human, the inner and outer shells providing in combination a cumulative corrective support greater than provided by either the inner shell or the outer shell by itself, the inner and outer shells being separable portions of the corrective device and not secured together and disconnectable from each other when not in use, the outer shell further shaped to accommodate positioning into the footwear for coupling with the footwear, the outer shell being a continuous contoured form without articulation joints or selectable adjustments during use, the inner shell and the outer shell being configured for removable insertion of the inner shell with the portion of the human therein into the outer shell to form a support assembly insertable into the footwear for wear by the human within the footwear and for removal of the inner shell with the portion of the human therein from within the outer shell for subsequent removal of the portion of the human from the inner shell, the inner shell and the outer shell being sized and shaped such that when the inner shell is coupled with the portion of the human and the outer shell is within the inner shell and the outer shell is positioned in the footwear, at least a portion of a pressure is distributed by the outer shell and the inner shell to the portion of the human to provide correction to the misalignment of the portion of the human.

49. A strapless corrective device to be worn on at least a portion of a foot of a human and to be positioned inside of a footwear while on the foot, the portion of the foot at least having a misalignment, the corrective device comprising:

an inner shell and an outer shell, the inner shell having an inner shell support wall with a upwardly opening elongated gap having a width smaller than the width of the foot, the inner shell support wall being sufficiently flexibility to permit selected temporary expansion thereof for passage of the foot through the inner shell support wall gap, the inner shell support wall extending away from the inner shell support wall gap being formed as an uninterrupted separate first unit having a continuous contoured form without articulation joints or selectable adjustments during use, and the outer shell having an outer shell support wall with a upwardly opening elongated gap having a width smaller than the foot, the outer shell support wall being sufficiently flexibility to permit selected temporary expansion thereof for passage of the foot with the inner shell thereon through the outer shell support wall gap, the outer shell support wall extending away from the outer shell support wall gap being formed as an uninterrupted separate second unit having a continuous contoured form without articulation joints or selectable adjustments during use, the inner shell shaped to accommodate receiving therein and supportingly couple with the portion of the foot, the inner shell having a shape and a first rigidity sufficient to move and hold the foot in a corrected position by applying a pressure to the portion of the foot to in part control the biomechanical positioning and alignment of the portion of the foot, and the outer shell shaped to accommodate removably receiving therein the inner shell with the portion of the foot therein and to fit within the footwear, the outer shell having a shape and a second rigidity to apply a pressure to the portion of the foot to in part control the biomechanical positioning and alignment of the portion of the foot, the inner and outer shells being separable portions of the corrective device unsecured to each other and disconnectable from each other when not in use while configured to jointly provide pressure to the portion of the foot for correction of the misalignment of the portion of the foot through only the support provided to the portion of the foot resulting from their rigidity without use of straps, the inner shell and the outer shell being sized and shaped such that the combined pressures applied by the inner shell and the outer shell to the portion of the foot provide correction to the misalignment of the portion of the foot.

\* \* \* \* \*

UNITED STATES PATENT AND TRADEMARK OFFICE
CERTIFICATE OF CORRECTION

| | | |
|---|---|---|
| PATENT NO. | : 7,618,387 B2 | Page 1 of 1 |
| APPLICATION NO. | : 11/351872 | |
| DATED | : November 17, 2009 | |
| INVENTOR(S) | : Donald R. Buethorn | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 294 days.

Signed and Sealed this

Twenty-sixth Day of October, 2010

David J. Kappos
*Director of the United States Patent and Trademark Office*

UNITED STATES PATENT AND TRADEMARK OFFICE
CERTIFICATE OF CORRECTION

PATENT NO. : 7,618,387 B2
APPLICATION NO. : 11/351872
DATED : November 17, 2009
INVENTOR(S) : Donald R. Buethorn Page 1 of 1

It is certified that error appears in the above-identified patent and that said Letters Patent is hereby corrected as shown below:

Column 20, lines 55 and 56 should read:
providing an outer shell having a second material the
composition substantially the same as the first material com- Signed and Sealed this
Twenty-ninth Day of May, 2012

David J. Kappos
*Director of the United States Patent and Trademark Office*